United States Patent
Rau et al.

(10) Patent No.: US 9,173,953 B2
(45) Date of Patent: Nov. 3, 2015

(54) PRODRUGS CONTAINING AN AROMATIC AMINE CONNECTED BY AN AMIDO BOND TO A LINKER

(75) Inventors: Harald Rau, Dossenheim (DE); Julia Baron, Heidelberg (DE); Ulrich Hersel, Fritz-Frey-Strasse (DE); Mathias Krusch, Hirschhorn (DE)

(73) Assignee: Ascendis Pharma AS, Hellerup (DK)

( * ) Notice: Subject to any disclaimer, the term of this patent is extended or adjusted under 35 U.S.C. 154(b) by 469 days.

(21) Appl. No.: 13/387,981

(22) PCT Filed: Jul. 30, 2010

(86) PCT No.: PCT/EP2010/061163
§ 371 (c)(1),
(2), (4) Date: Mar. 6, 2012

(87) PCT Pub. No.: WO2011/012722
PCT Pub. Date: Feb. 3, 2011

(65) Prior Publication Data
US 2012/0156260 A1 Jun. 21, 2012

(30) Foreign Application Priority Data
Jul. 31, 2009 (EP) .................................. 09167029

(51) Int. Cl.
| | | |
|---|---|---|
| *A61K 31/428* | (2006.01) | |
| *A61K 9/14* | (2006.01) | |
| *A61P 25/24* | (2006.01) | |
| *A61P 25/00* | (2006.01) | |
| *A61P 25/16* | (2006.01) | |
| *A61K 47/48* | (2006.01) | |

(52) U.S. Cl.
CPC ....... *A61K 47/48315* (2013.01); *A61K 47/4823* (2013.01); *A61K 47/48215* (2013.01); *A61K 47/48338* (2013.01)

(58) Field of Classification Search
None
See application file for complete search history.

(56) References Cited

U.S. PATENT DOCUMENTS

| 6,455,268 B1 | 9/2002 | Jarnigan et al. |
|---|---|---|
| 2004/0063628 A1 | 4/2004 | Piccariello et al. |
| 2005/0054612 A1 | 3/2005 | Monahan et al. |

FOREIGN PATENT DOCUMENTS

| EP | 1625856 | 2/2006 |
|---|---|---|
| WO | WO 99/30727 | 6/1999 |
| WO | WO 2004/108070 | 12/2004 |
| WO | WO 2005/099768 | 10/2005 |
| WO | WO 2006/003014 | 1/2006 |
| WO | WO 2006/136586 | 12/2006 |
| WO | WO 2006/138572 | 12/2006 |
| WO | WO 2007/019331 | 2/2007 |
| WO | WO 2008/006102 | 1/2008 |
| WO | WO 2008/082613 | 7/2008 |
| WO | WO 2009/095479 | 8/2009 |

OTHER PUBLICATIONS

Ellman et al., "A New and Rapid Colorimetric Determination of Acetylcholinesterase Activity", Biochemical Pharmacology, 1961, pp. 88-95, vol. 7, Pergamon Press Ltd., Great Britain.

Bonnet et al., "Solid-Phase Organic Tagging Resins for Labeling Biomolecules by 1,3-Dipolar Cycloaddition to the Synthesis of a Fluorescent Non-Peptidic Vasopressin Receptor Ligand", Chem. Eur. J., 2008, pp. 6247-6254, vol. 14, Wiley-VCH Verlag GmbH &Co., KGaA, Weinheim, Germany.

Greenwald et al., "Drug Delivery Systems Employing 1,4- or 1,6-Elimination: Poly(ethylene glycol) Prodrugs of Amine-Containing Compounds", J. Med. Chem., 1999, pp. 3657-3667, vol. 42, American Chemical Society, U.S.

Hennard et al., "Synthesis and Activities of Pyoverdin-Quinolone Adducts: A Prospective Approach to a Specific Therapy Against *Pseudomonas aeruginosa*", J. Med. Chem., 2001, pp. 2139-2151, vol. 44, American Chemical Society, U.S.

English et al., "Orally Effective Acid Prodrugs of the β-Lactamase Inhibitor Sulbactam", J. Med. Chem., 1990, pp. 344-347, vol. 33, American Chemical Society, U.S.

Li et al., "Chemical Adaptor Immunotherapy: Design, Synthesis, and Evaluation of Novel Integrin-Targeting Devices", J. Med. Chem., 2004, pp. 5630-5640, vol. 47, American Chemical Society, U.S.

Jenkem Technology USA Product List, Apr. 2009.

*Primary Examiner* — Kamal Saeed
(74) *Attorney, Agent, or Firm* — Frommer Lawrence & Haug

(57) ABSTRACT

The present invention relates to a prodrug or a pharmaceutically acceptable salt thereof comprising a drug linker conjugate D-L, wherein an aromatic amine containing biologically active moiety is connected (bound) by an amido bound to a linker. The invention also relates to pharmaceutical compositions comprising said prodrugs and their use as medicaments.

20 Claims, 1 Drawing Sheet

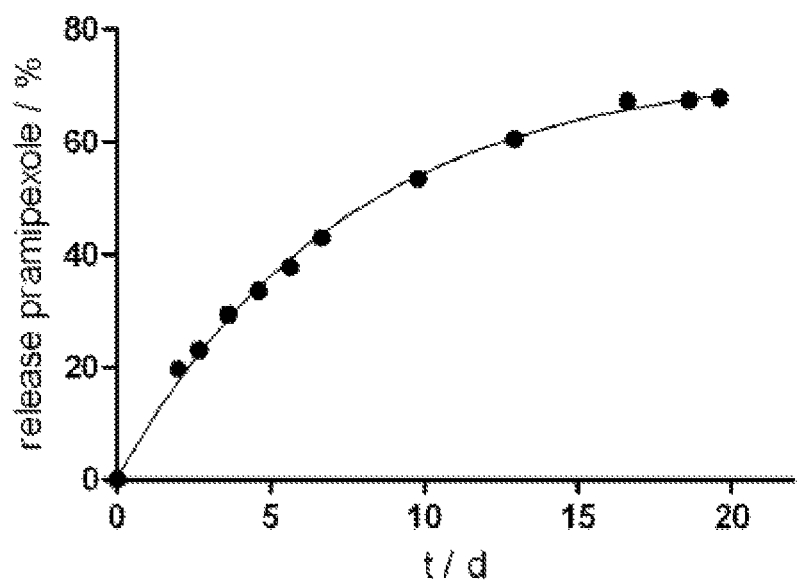

PRODRUGS CONTAINING AN AROMATIC AMINE CONNECTED BY AN AMIDO BOND TO A LINKER

The present invention relates to a prodrug or a pharmaceutically acceptable salt thereof, comprising a drug linker conjugate D-L, wherein an aromatic amine containing biologically active moiety is connected (bound) by an amido bond to a linker. The invention also relates to pharmaceutical compositions comprising said prodrugs and their use as medicaments.

To enhance physicochemical or pharmacokinetic properties of a drug in vivo, such drug can be conjugated with a carrier. If the drug is chemically bound to a carrier and/or a linker, such systems are commonly assigned as prodrugs. According to the definitions provided by IUPAC (as given under http://www.chem.qmul.ac.uk/iupac.medchem, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs may be transient, meaning that they are non-enzymatically hydrolytically degradable (cleavable) under physiological conditions (aqueous buffer at pH 7.4, 37° C.) with half-lives ranging from, for example, one hour to three months. On the other hand, stable linkages such as employed in connecting moieties and spacer, are typically non-cleavable permanent bonds, meaning that the respective spacer or connecting moiety have a half-life of at least six months under physiological conditions (aqueous buffer at pH 7.4, 37° C.).

Suitable carriers are polymers or $C_{8-18}$ alkyl groups and can either be directly conjugated to the linker or via a non-cleavable spacer.

The term polymer describes a molecule comprised of repeating structural units connected by chemical bonds in a linear, circular, branched, crosslinked or dendrimeric way or a combination thereof, which can be of synthetic or biological origin or a combination of both.

In addition to carrier-linked prodrugs, drugs can also be bound to carriers in a non-covalent way, using physicochemical formulations of drug-solvent-carrier mixtures. However, the non-covalent approach requires a highly efficient drug encapsulation to prevent uncontrolled, burst-type release of the drug. Restraining the diffusion of an unbound, water soluble drug molecule requires strong van der Waals contacts, frequently mediated through hydrophobic moieties. Many conformationally sensitive drugs, such as proteins or peptides, are rendered dysfunctional during the encapsulation process and/or during subsequent storage of the encapsulated drug. In addition, such amino-containing drugs readily undergo side reactions with carrier degradation products. Furthermore, dependence of the release mechanism of the drug upon biodegradation may cause interpatient variability.

Alternatively, the drugs may be conjugated to a carrier via a transient linker molecule (carrier-linked prodrugs). This approach is applied to various classes of molecules, from so-called small molecules, through natural products up to larger proteins. This approach is applied to various classes of molecules, from so-called small molecules, through natural products up to larger proteins.

Prodrug activation may occur by enzymatic or non-enzymatic cleavage of the bond between the carrier and the drug molecule, or a sequential combination of both, i.e. an enzymatic step followed by a non-enzymatic rearrangement.

Enzymatically induced prodrug activation is characterized in that the cleavage in enzyme-free in-vitro environment such as an aqueous buffer solution, of, e.g., an ester or amide may occur, but the corresponding rate of hydrolysis may be much too slow and not therapeutically useful. In an in-vivo environment, esterases or amidases are typically present and the esterases and amidases may cause significant catalytic acceleration of the kinetics of hydrolysis from twofold up to several orders of magnitude. Therefore, the cleavage is predominantly controlled by the enzymatic reaction.

A major drawback of predominantly enzymatic cleavage is interpatient variability. Enzyme levels may differ significantly between individuals resulting in biological variation of prodrug activation by the enzymatic cleavage. The enzyme levels may also vary depending on the site of administration. For instance it is known that in the case of subcutaneous injection, certain areas of the body yield more predictable therapeutic effects than others. To reduce this unpredictable effect, non-enzymatic cleavage or intramolecular catalysis is of particular interest.

Therefore, enzyme-independent autocatalytic cleavage of carrier and biologically active moiety is preferred. In most cases this is achieved by an appropriately designed linker moiety between the carrier and the biologically active moiety, which is directly attached to the functional group of a biologically active moiety via covalent bond.

Numerous bioactive substances (drugs) contain an aromatic amine moiety. For instance, aniline derivatives are characterized by an amine connected to an aromatic ring. It has been subject of research to generate prodrugs of aniline derivatives to improve on therapeutic properties of said drug (parent compound). By consequence, aromatic amides, such as anilides, i.e. compoundes whose aromatic amino group is converted into an amide in order to form a prodrug, are of interest. However, the type of linker of a prodrug strongly influences the release rate of the aromatic amine by cleavage of the aromatic amide fragment of such a prodrug.

Specific linker types are known in the art. For example, in WO-A 2004/108070 there is, among others, a prodrug system based on a N,N-bis-(2-hydroxyethyl)glycine amide (bicine) linker described. In this system two PEG carrier molecules are linked to a bicine molecule coupled to, for example, an amino group of the drug molecule. By consequence, the linker only contains one amide bond, which may be aromatic depending on the respective drug molecule employed. In addition, the linker does not contain a secondary amido fragment, but a tertiary amino function instead due to the employment of a N,N-substituted spacer component. The first step in prodrug activation is the enzymatic cleavage of the first linkages connecting both PEG carrier molecules with the hydroxy groups of the bicine activating group. Different linkages between PEG and bicine are described resulting in different prodrug activation kinetics. The second step in prodrug activation is the cleavage of the second linkage connecting the bicine activating group to the amino group of the drug molecule. Consequently the release of a bicine-modified prodrug intermediate may show different pharmacokinetic, immunogenic, toxicological and pharmacodynamic properties as compared to the parent native drug molecule. Another comparable bicine-based system is described in WO-A 2006/136586.

The international application PCT/EP2009/051079 also discloses prodrugs containing a different linker type. Said prodrug comprises a drug linker conjugate, wherein the linker is connected to a carrier group. The linker contains a non-biologically active linker moiety $L^1$, which is chemically bound to the nitrogen of the biologically active moiety by forming an amide bond. The linker moiety $L^1$ mandatorily contains 2 amino functions, which are connected by an alkyl fragment containing 2 or 3 carbon atoms.

Another linker system is described in US 2005/0054612, which relates to drug formulations that increase regional delivery of the drugs to the cells. The respective drug is covalently linked to one or more hydrophobic moieties via one or more labile bonds. Said labile bond, which is preferably hydrolytically labile, may be silazane or maleamic acid. One of the drugs disclosed (propidium iodide) contains an aromatic amine, which is reacted with the respective methyl-maleic anhydride to build up a modified drug containing a dodecyl amine connected to propidium iodide by a maleamic acid linker. Said maleamic acid linker is branched and contains a spacer of three carbon atoms between the respective carbon atoms of the two amido groups. However, the half-life of said maleimic anilide (aromatic amine containing a drug connected to the maleamic acid linker) is short in buffered solution at pH of 7.2 (6.1 sec), which is explained by the low pKa of the aniline type nitrogens on propodium iodide.

C. Hennard et al., J. Med. Chem. 2001, 44, pages 2139-2151 discloses specific linkers based on succinic acid fragments. The respective spacers contain 2 succinic acid fragments connected by an ethylene diamine bridge. One linker additionally contains a methylenedioxy group. By consequence, each linker contains 4 amide bonds. Each linker is bound on one side to a pyoverdin backbone and on the other side to a specific quinolone drug by an aliphatic amide bond. It was found that the linker which additionally contains the methylenedioxy group is gradually hydrolysable, whereas the other linker is stable. By consequence, the adducts (prodrugs, with the hydrolysable spacer arm) are recommended to be employed as pharmaceuticals for the therapy against *Pseudomonas aeruginosa*, since they have a better activity than those compounds with the stable spacer, wherein the quinolone is directly bound to the succinic acid fragment of the respective linker.

WO 2006/138572 discloses conjugates having a degredable linkage and polymeric reagents useful in preparing such conjugates. The conjugates contain a polypeptide as an active agent, the polymeric reagent is based on an aromatic containing moiety, such a fluorene, being bound via two spacers to two water-soluble polymers. The spacer comprises, among others, glutaric acid fragments, which may form amido bonds with the aromatic containing moiety. The spacer fragment of the polymeric reagent according to WO 2006/138572 is found to be stable, the degreadable linkage within the conjugate is a, for example, —O—C(O)—NH-bridge connecting the polypeptide with the aromatic containing moiety originating from the polymeric reagent. Said aromatic containing fragment is, however, part of a non-biologically active linker for connecting the polymers with the polypeptide (active agent).

However, linkers based on succinic acid are also known to be employed in different applications. U.S. Pat. No. 6,455, 268 discloses compounds and methods for detecting and assaying enzyme activity in an intact cellular system. Said compounds contain a linking moiety for connecting a fluorescent donor moiety with a fluorescent acceptor moiety. The linker may contain a fragment based on succinic acid containing an aromatic and an aliphatic amide bond. The fluorescent acceptor moiety is connected to the linker via an aromatic amide. However, it is not reported that said fluorescent acceptor moiety can be employed as a drug. Instead, the respective amide bond has to be very stable, since said compound has to be used as a fluorescent substrate for the detection of enzyme activities in vivo.

Accordingly, there is a need for alternative carrier-linked prodrugs, where the linker allows an autocatalytic cleavage to release a drug with a controlled release rate and in an unmodified form without remaining residues originating from the linker.

Thus, an object of the present invention is to provide such drug linker conjugates, where the linker is covalently attached via a cleavable bond to a biologically active moiety (representing the drug after release), and where the linker is further covalently attached via a permanent bond to a carrier directly or via a spacer to form the carrier-linked prodrug.

This object is achieved by a prodrug or a pharmaceutically acceptable salt thereof comprising a drug linker conjugate D-L, wherein D is an aromatic amine containing biologically active moiety; and L is a non-biologically active linker containing
i) a moiety $L^1$ represented by formula (I),

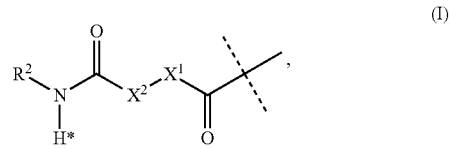

wherein the dashed line indicates the attachment of $L^1$ to an aromatic amino group of D by forming an amide bond;

$X^1$ is $C(R^1R^{1a})$ or a cyclic fragment selected from $C_{3-7}$ cycloalkyl, 4 to 7 membered heterocyclyl, phenyl, naphthyl, indenyl, indanyl, tetralinyl, or 9 to 11 membered heterobicyclyl, wherein in case $X^1$ is a cyclic fragment, said cyclic fragment is incorporated into $L^1$ via two adjacent ring atoms and the ring atom of $X^1$, which is adjacent to the carbon atom of the amide bond, is also a carbon atom;

$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, or O—$C(R^3R^{3a})$, wherein in case $X^1$ is a cyclic fragment, $X^2$ is a chemical bond, $C(R^3R^{3a})$, $N(R^3)$ or O;

optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;

$R^1$, $R^3$ and $R^4$ are independently selected from the group consisting of H, $C_{1-4}$ alkyl and —$N(R^5R^{5a})$;

$R^{1a}$, $R^2$, $R^{3a}$, $R^{4a}$ and $R^{5a}$ are independently selected from the group consisting of H, and $C_{1-4}$ alkyl;

$R^5$ is $C(O)R^6$;

$R^6$ is $C_{1-4}$ alkyl;

optionally, one of the pairs $R^{1a}/R^{4a}$, $R^{3a}/R^{4a}$ or $R^{1a}/R^{3a}$ form a chemical bond; and ii) a moiety $L^2$, which is a chemical bond or a spacer, and $L^2$ is bound to a polymeric carrier group Z, wherein $L^1$ is substituted with one to four $L^2$ moieties, provided that the hydrogen marked with the asterisk in formula (I) is not replaced by $L^2$;

optionally, L is further substituted.

It was surprisingly found that prodrugs comprising a drug linker conjugate D-L containing a linker moiety $L^1$, as defined above, exhibit therapeutically useful autohydrolysis (autocatalytic cleavage) if linked to an aniline derivative or an other type of aromatic amine through an anilide bond or an amide bond, respectively. This finding is strongly influenced by the chemical nature of said linker moiety $L^1$, which has a first (aliphatic) amide bond (due to the substituent $R^2$) and (under the perspective of the uncleaved drug linker conjugative D-L) a second (aromatic) amide bond. Between the two amide bonds there is a spacer ($X^2$-$X^1$-fragment), which keeps the respective carbonyl atoms of the two amido groups (of $L^1$) in β or γ-position to each other.

By consequence, the prodrugs according to the present invention show the beneficial effect of a controlled release rate in respect of the (cleaved) drug D-H. Preferably, a sustained release rate can be obtained. Sustained release (rate) means that the administration intervals of the respective prodrug are expanded. Instead of a commonly one or three times daily dosage form, a (for example) once weekly dosage form (or even longer administration intervals) can be applied to a person in need thereof.

The prodrug according to the present invention show excellent in vivo/in vitro correlation of linker cleavage, a high degree of enzyme independence and show a higher stability at lower pH (pH dependent cleavage).

Within the present invention the terms are used having the meaning as follows.

A strong in vivo/in vitro correlation is observed, if the release kinetics exhibited by a carrier-linked prodrug conjugate according to the invention in vivo (plasma levels of free drug) has a half-life that is not smaller than half the value exhibited by the same carrier-linked prodrug conjugate in aqueous buffer of pH 7.4 at 37° C. It is understood that in the case of soluble carriers, release kinetics may be recorded as a hydrolysis kinetics.

"Aromatic amine containing biologically active moiety D" means the part (moiety or fragment) of the drug linker conjugate D-L, which results after cleavage in a drug D-H (active agent) of (known) biological activity. In addition, the subterm "aromatic amine containing" means that the respective moiety D and analogously the corresponding drug D-H contain at least one aromatic fragment, which is substituted with at least one amino group. The terms "drug" and "biologically active moiety" are used synonymously.

The amino substituent of the aromatic fragment of D forms together with the carbonyl-fragment (—C(O)—) on the right hand side of $L^1$ (as depicted in formula (I)) an amide bond within the drug linker conjugate D-L. By consequence, the two parts D and L of the drug linker conjugate D-L are connected (chemically bound) by an amide fragment of the general structure $Y^1$—C(O)—N(R)—$Y^2$. $Y^1$ indicates the remaining parts of the moiety $L^1$ and $Y^2$ indicates the aromatic fragment of D. R is a substituent such as $C_{1-4}$ alkyl or preferably hydrogen. For example, said amide bond is indicated within formula (I) by the dashed line added diagonally on this bond.

"Non-biologically active linker" means a linker which does not show the pharmacological effects of the drug (D-H) derived from the biologically active moiety.

As indicated above, the $X^1$-fragment of the moiety $L^1$ represented by formula (I) may also be a cyclic fragment such as $C_{3-7}$ cycloalkyl, phenyl or indanyl. In case $X^1$ is such a cyclic fragment, the respective cyclic fragment is incorporated into $L^1$ via two adjacent ring atoms (of said cyclic fragment). For example, if $X^1$ is phenyl, the phenyl fragment of $L^1$ is bound to the $X^2$ fragment of $L^1$ via a first (phenyl) ring atom being in α-position (adjacent) to a second (phenyl) ring atom, which itself is bound to the carbon atom of the carbonyl-fragment on the right hand side of $L^1$ according to formula (I) (the carbonyl fragment which forms together with the aromatic amino group of D an amide bond).

"Alkyl" means a straight-chain or branched carbon chain (unsubstituted alkyl). Optionally, each hydrogen of an alkyl carbon may be replaced by a substituent.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —CH($CH_3$)—, —$CH_2$—$CH_2$—$CH_2$—, —CH($C_2H_5$)—, —C($CH_3$)$_2$—, when two moieties of a molecule are linked by the alkyl group. Optionally, each hydrogen of a $C_{1-4}$ alkyl carbon may be replaced by a substituent. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms (unsubstituted $C_{2-50}$ alkenyl), e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Optionally, each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms (unsubstituted $C_{2-50}$ alkynyl), e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Optionally, each hydrogen of a $C_{2-50}$ alkynyl carbon may be replaced by a substituent as further specified. Accordingly, the term "alkynyl" relates to a carbon chain with at lest one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated (unsubstituted $C_{3-7}$ cycloalkyl), e.g. cyclopropyl, cyclobutyl, cyclopentyl, cyclohexyl, cyclohexenyl, cycloheptyl. Optionally, each hydrogen of a cycloalkyl carbon may be replaced by a substituent. The term "$C_{3-7}$ cycloalkyl" or "$C_{3-7}$ cycloalkyl ring" also includes bridged bicycles like norbonane (norbonanyl) or norbonene (norbonenyl). Accordingly, "$C_{3-5}$ cycloalkyl" means a cycloalkyl having 3 to 5 carbon atoms.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or unsaturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 4 to 7 membered heterocyclyl). For the sake of completeness it is indicated that, for example, in case $X^1$ is 4 to 7 membered heterocyclyl, the respective additional requirements of $X^1$ have to be considered as well. This means that in this case the respective 4 to 7 membered heterocyclyl is incorporated into $L^1$ via two adjacent ring atoms and the ring atom of said 4 to 7 membered heterocyclyl, which is adjacent to the carbon atom of the amide bond, is also a carbon atom.

Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, each hydrogen of a 4 to 7 membered heterocyclyl may be replaced by a substituent.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 9 to 11 membered heterobicyclyl). For the sake of completeness it is indicated that, for example, in case $X^1$ is 9 to 11 membered heterobicyclyl, the respective additional requirements of $X^1$ have to be considered as well. This means that in this case the respective 9 to 11 membered heterobicyclyl is incorporated into $L^1$ via two adjacent ring atoms and the ring atom of said 9 to 11 membered heterobicyclyl, which is adjacent to the carbon atom of the amide bond, is also a carbon atom.

Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane. Optionally, each hydrogen of a 9 to 11 membered heterobicyclyl may be replaced by a substituent.

In case the prodrugs according to the present invention contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts of the prodrugs of the present invention can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

"Pharmaceutical composition" means a composition containing one or more active ingredients (for example a drug or a prodrug), and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a prodrug of the present invention and a pharmaceutically acceptable excipient. The term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic (drug or active ingredient), preferably in purified form, together with a suitable amount of excipient so as to provide the form for proper administration to the patient. The formulation should suit the mode of administration.

The term "reagent" refers to an intermediate or starting material used in the assembly process leading to a prodrug of the present invention.

The term "chemical functional group" refers to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

A "degradable interconnected functional group" is a linkage comprising a biodegradable bond which on one side is connected to a spacer moiety connected to a backbone moiety and on the other side is connected to the crosslinking moiety. The terms "degradable interconnected functional group", "biodegradable interconnected functional group", "interconnected biodegradable functional group" and "interconnected functional group" are used synonymously.

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups.

The term "interconnectable functional group" refers to chemical functional groups, which participate in a radical polymerization reaction and are part of the crosslinker reagent or the backbone reagent.

The term "polymerizable functional group" refers to chemical functional groups, which participate in a ligation-type polymerization reaction and are part of the crosslinker reagent and the backbone reagent.

A backbone moiety may comprise a spacer moiety which at one end is connected to the backbone moiety and on the other side to the crosslinking moiety.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

"Non-biologically active linker" means a linker which does not show the pharmacological effects of the drug (D-H) derived from the biologically active moiety.

The terms "spacer", "spacer group", "spacer molecule", and "spacer moiety" are used interchangeably and if used to describe a moiety present in the hydrogel carrier of the invention, refer to any moiety suitable for connecting two moieties, such as C1-50 alkyl, C2-50 alkenyl or C2-50 alkinyl, which fragment is optionally interrupted by one or more groups selected from —NH—, —N(C1-4 alkyl)-, —O—, —S—, —C(O)—, —C(O)NH—, —C(O)N(C1-4 alkyl)-, —O—C(O)—, —S(O)—, —S(O)2-, 4 to 7 membered heterocyclyl, phenyl or naphthyl.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for backbone reagents, backbone moieties, crosslinker reagents, and crosslinker moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The term "poly(ethylene glycol) based polymeric chain" or "PEG based chain" refers to an oligo- or polymeric molecular chain.

Preferably, such poly(ethylene glycol) based polymeric chain is connected to a branching core, it is a linear poly(ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

If the term "poly(ethylene glycol) based polymeric chain" is used in reference to a crosslinker reagent, it refers to a crosslinker moiety or chain comprising at least 20 weight % ethylene glycol moieties.

In the following, the present invention is explained in more detail.

D is an aromatic amine containing biologically active moiety. D may be any aromatic amine containing biologically active moiety known to a person skilled in the art, which is derived from the corresponding biologically active drug D-H obtained after cleavage of D from the drug linker conjugate D-L (D-His the drug or active agent obtained after release from D-L). As indicated above, D contains at least one aromatic fragment, which is substituted with at least one amino group and said amino group is in turn connected to the moiety $L^1$ by forming an amide bond.

The amide bond may be attached to any carbon atom of suitable substructures of D, including, but not limited to, thiophenes, pyrroles, imidazoles, pyrazoles, oxazoles, isoxazoles, thiazoles, isothiazoles, thiadiazoles, thiadiazolines, pyrans, pyridazines, pyrazines, pyrimidines and tetrazoles.

D may contain further substituents—besides at least one aromatic amino group—such as alkyl or halogen. The term "aromatic" (aromatic fragment) means any aromatic fragment known to a person skilled in the art such as aryl (for example, phenyl or naphthyl) or heteroaryl (for example, aromatic 4 to 7 membered heterocyclyl or aromatic 9 to 11 membered heterobicyclyl). The aromatic fragment comprises mono-, bi- or polycyclic fragments. In case of bi- or polycyclic fragments it is sufficient that only one of said cycles is aromatic. D may contain two or more further aromatic fragments as defined before, which are bound to the first aromatic fragment, which is substituted with at least one amino group, either directly by a chemical bound or by a spacer. Said two or more additional aromatic fragments may also contain at least one amino group. In the following, D is defined by the corresponding biologically active drug D-H.

D-His preferably selected from the group consisting of Abacavir, Acadesine, Acediasulfone, Aciclovir, Actimid, Actinomycin, Adefovir, Aditeren, Afloqualone, Aztreonam, Adefovir Dipivoxil, Adenine, Adenosine, Adenosine monophosphate, Adenosine triphosphate, Alfuzosin, Alpiropride, Ambasilide, Ambucaine, Ameltolide, Amethopterin, Amicycline, Amidapsone, Amiloride, Aminoacridine, Aminoantipyrine, Aminobenzoate, 6-Aminoflavone, 17-Aminogeldanamycin, Aminogenistein, Aminoglutethimide, Aminohippurate, 3'-Amino-4'-methoxyflavone, Aminonimetazepam, Aminopotentidine, Amphenidone, N-(p-Aminophenethyl)spiroperidol, 2-Amino-6(5H)-phenanthridinone, Amiphenosine, Aminophenylalanine, Aminopterin, Aminopurvalanol A, Amfenac, Amiphenazole, Amphotalide, Aminoisatin, Aminosalicylic Acid, Amifampridine, Amisulpride, Amlexanox, Amonafide, Amprenavir, Amrinone, Amthamine, Anileridine, Apraclonidine, Ascensil, Atolide, Azabon, Azacitidine, Azepexole, Aztreonam, Basedol, Benzocaine, Batanopride, Betoxycaine, Bleomycin, Bromfenac, Bromobuterol, Bromopride, Carbutamide, Carumonam, Candicidin, Cefepime, Cefcapene pivoxil, Cefdaloxime, Cefdinir, Cefditoren, Cefempidone, Cefetamet, Cefepime, Cefetecol, Cefixime, Cefmatilen, Cefmenoxime, Cefodizime, Cefoselis, Cefotaxime, Cefotiam, Ceftiolene, Ceftioxide, Cefpodoxime, Cefquinome, Cefrom, Ceftazidime, Cefteram, Ceftibuten, Ceftiofur, Ceftizoxime, Ceftriaxone, Cefuzonam, Cisapride, Clenproperol, Chloroprocaine, Cidofovir, Cisapride, Cladribine, Clafanone, Claforan, Clebopride, Clenbuterol, Clofarabine, Clorsulon, Cycloclenbuterol, Cytarabine, Cytidoline, Dactinomycin, Daniquidone, Dactinomycin, Dapsone, Daptomycin, Daraprim, Darunavir, Dazopride, Decitabine, Declopramide, Diaminoacridine, Dichlorophenarsine, Dimethocaine, 10'-Demethoxystreptonigrin, 2,7-Dimethylproflavine, Dinalin, Dobupride, Doxazosin, Draflazine, Emtricitabine, Entecavir, Ethacridine, Etanterol, Etoxazene, Famciclovir, Fepratset, (±)-FLA 668, Flucytosine, Fludarabine, Folic Acid, Fosamprenavir, Ganciclovir, Gemcitabine, Gloximonam, GSK 3B Inhibitor XII, Glybuthiazol, Hydroxymethylclenbuterol, Hydroxyprocaine, Imiquimod, Indanocine, Iomeglamic acid, Iramine, Isobutamben, Isoritmon, Ketoclenbuterol, Lamivudine, Lamotrigine, Lavendamycin, Lenalidomide, Leucinocaine, Leucovorin, Lintopride, Lisadimate, Mabuterol, Medeyol, Mesalazine, Metabutethamine, Metabutoxycaine, Metahexamide, Methyl anthranilate, Methotrexate, Metoclopramide, Minoxidil, Mirabegron, Mitomycin, Mocetinostat, Monocain, Mosapride, NADH, Mutamycin, Naepaine, Naminterol, Nelarabine, Nepafenac, Nerisopam, Nitrine, Nomifensine, Norcisapride, Olamufloxacin, Orthocaine, Oxybuprocaine, Oximonam, Pancopride, Parsalmide, Pathocidine, Pasdrazide, Pemetrexed, Penciclovir, Phenazone, Phenazopyridine, Phenyl-PAS-Tebamin, Picumeterol, Pirazmonam, Porfiromycin, Pramipexole, Prazosin, Piridocaine, Procainamide, Procaine, Proflavine, N-Propionylprocainamide, Proparacaine, Propoxycaine, Prucalopride, Pyrimethamine, Questiomycin, Renoquid, Renzapride, Retigabine, Riluzole, Rufocromomycin, S-Adenosylmethionine, Silver sulfadiazine, Sparfloxacin, Stearylsulfamide, Streptonigrin, Succisulfone, Sulamserod, Sulfabromomethazine, Sulfacetamide, Sulfaclozine, Sulfaclorazole, Sulfachlorpyridazine, Sulfachrysoidine, Sulfaclomide, Sulfacytine, Sulfadiasulfone, Sulfadimethoxine, Sulfadimidine, Sulfadicramide, Sulfadiazine, Sulfadoxine, Sulfaguanidine, Sulfaguanole, Sulfalene, Sulfamerazine, Sulfamethazine, Sulfanilamidoimidazole, Sulfanilylglycine, N-Sulfanilylnorfloxacin, Sulfathiadiazole, Sulfamethizole, Sulfamethoxazole, Sulfametopyrazine, Sulfapyrazole, Sulfamethoxydiazine, Sulfasymazine, Sulfatrozole, Sulfatroxazole, Sulfamethoxypyridazine, Sulfametomidine, Sulfametrole, Sulfamonomethoxine, Sulfanilamide, Sulfaperin, Sulfaphenazole, Sulfaproxyline, Sulfapyridine, Sulfisomidine, Sulfasomizole, Sulfisoxazole, Suprax, Tacedinaline, Tacrine, Talampanel, Talipexole, Tenofovir, Terazosin, Tetrahydrobiopterin, Tetrahydrofolic acid, Thiamine, Thiazosulfone, Thioguanine, Tigemonam, Timirdine, Trimethoprim, Triamterene, Trimethoprim, Trimetrexate, Tritoqualine, Valaciclovir, Valganciclovir, Veradoline, Vidarabine, Zalcitabine, and Zoxazolamine.

Most preferably, D-His pramipexole.

In one embodiment of the present invention, D (or D-H, respectively) does not contain a fluorenyl fragment substituted with the aromatic amino group. Aromatic amino group means that said group is attached in the drug linker conjugate D-L to the moiety $L^1$ by forming the amide bond.

The non-biologically active linker L contains a moiety $L^1$ represented by formula (I) as depicted and defined above. Preferably, the moiety $L^1$ is defined as follows.

$X^1$ is $C(R^1R^{1a})$, cyclohexyl, phenyl, pyridinyl, norbonenyl, furanyl, pyrrolyl or thienyl,
wherein in case $X^1$ is a cyclic fragment, said cyclic fragment is incorporated into $L^1$ via two adjacent ring atoms;

$X^2$ is a chemical bond or selected from $C(R^3R^{3a})$, $N(R^3)$, O, $C(R^3R^{3a})$—O or $C(R^3R^{3a})$—$C(R^4R^{4a})$;

$R^1$, $R^3$ and $R^4$ are independently selected from H, $C_{1-4}$ alkyl or —$N(R^5R^{5a})$;

$R^{1a}$, $R^{3a}$, $R^{4a}$ and $R^{5a}$ are independently selected from H or $C_{1-4}$ alkyl;

$R^2$ is $C_{1-4}$ alkyl;

$R^5$ is $C(O)R^6$;

$R^6$ is $C_{1-4}$ alkyl;

More preferably, the moiety $L^1$ is selected from

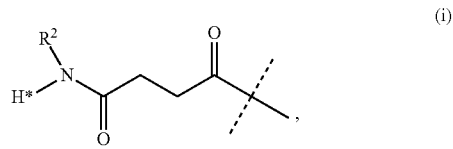

(i)

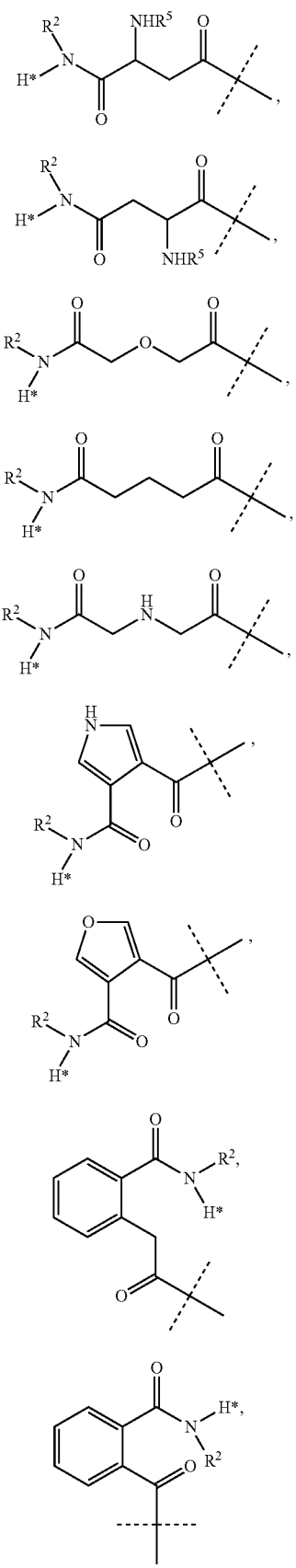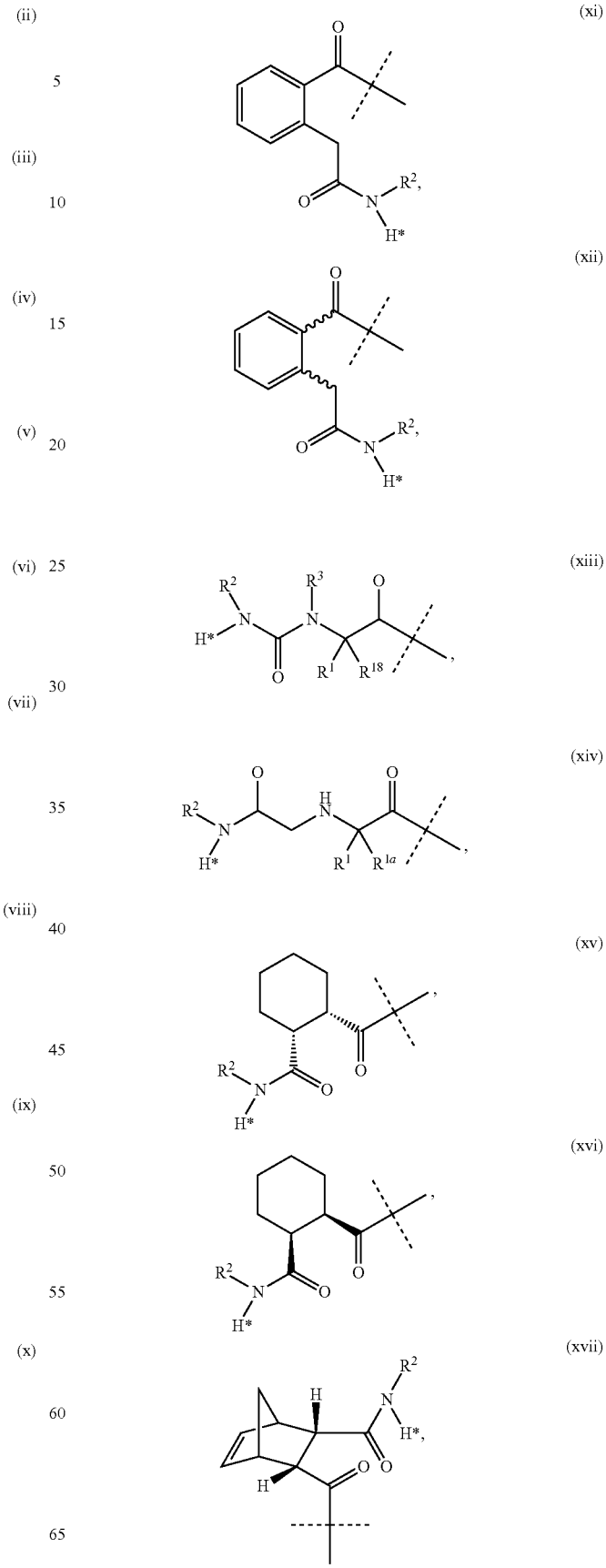

-continued (xviii) 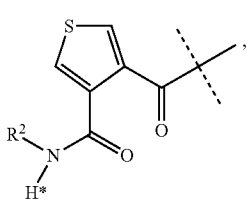

(xvix) 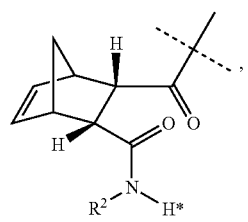

(xx) 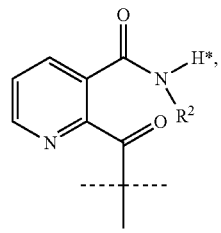

(xxi) 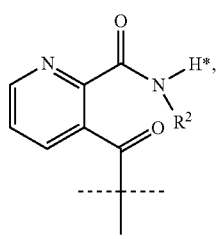

(xxii) 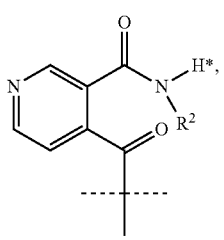

(xxiii) 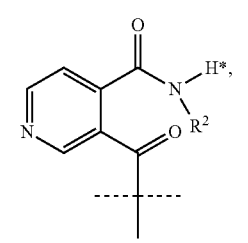

(xxiv) 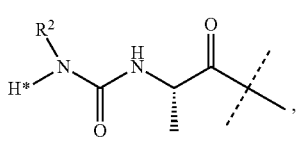

-continued (xxv) 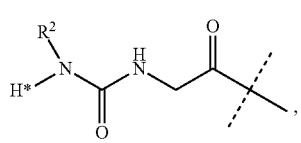

(xxvi) 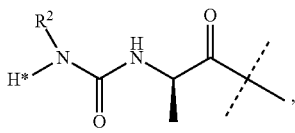

(xxvii) 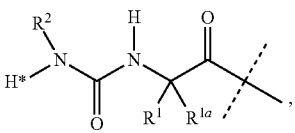

(xxviii) 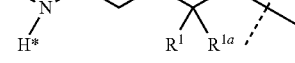

(xxix)

wherein
$R^5$ is $C(O)R^6$;
$R^1$, $R^{1a}$, $R^2$, $R^3$ and $R^6$ are independently from each other $C_{1-4}$ alkyl; and
$L^1$ is substituted with one $L^2$ moiety, preferably $R^2$ is substituted with one $L^2$ moiety.

In one embodiment of the present invention, the moiety $L^1$ is even more preferably (ii) 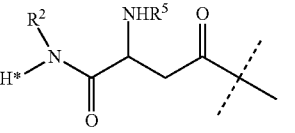

(iii) 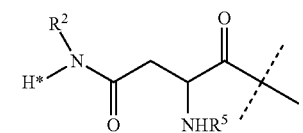

wherein
$R^5$ is $C(O)R^6$;
$R^6$ is $C_{1-4}$ alkyl; and
$R^2$ is substituted with one $L^2$.

In another embodiment of the present invention, the moiety $L^1$ is even more preferably

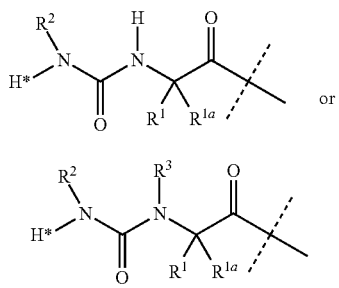

(xxvii)

or (xxviii)

wherein $R^1$, $R^{1a}$, $R^2$, and $R^3$ are independently from each other selected from H or $C_{1-4}$ alkyl; and $R^2$ is substituted with one $L^2$ moiety.

L also contains a moiety $L^2$, which is a chemical bond or a spacer. $L^2$ is bound to a carrier group Z. $L^1$ is substituted with 1 to 4 $L^2$ moieties, provided that the hydrogen marked with the asterisk in formula (I) is not replaced by $L^2$. In case more than one $L^2$ moiety is present, each $L^2$ and, by consequence, each Z can be selected independently. In general, $L^2$ can be attached to $L^1$ at any position apart from the replacement of the hydrogen marked with an asterisk in formula (I). The attachment of the respective $L^2$ moiety occurs by replacing one hydrogen according to the definitions of $X^1$, $X^2$, $R^1$ to $R^5$ and $R^{1a}$ to $R^{5a}$. Preferably, $L^1$ is substituted with one $L^2$ moiety. More preferably, $R^2$ is substituted with one $L^2$ moiety (the substitution occurs at the $R^2$ fragment of the moiety $L^1$). In particular, $R^2$ is substituted with $L^2$ at the terminal carbon atom, if $R^2$ is $C_{1-4}$ alkyl, preferably butyl.

In another embodiment, the moiety $L^2$ may entirely replace $R^2$ within formula (I) or the preferred definitions thereof, respectively.

In case $L^2$ is a spacer, any spacer known to a person skilled in the art for connecting a moiety $L^1$ as represented by formula (I) to a carrier can be used. Preferably, the spacer is a fragment selected from $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

More preferably, the spacer is a fragment selected from $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl, provided that the spacer does not contain a nitrogen atom being in β- or γ-position to the amino group containing the hydrogen marked with the asterisk in formula (I), in case the spacer is bound to $R^2$.

The term "interrupted" means that between two carbon atoms of the spacer or at the end of the carbon chain between the respective carbon atom and the hydrogen atom a group (as defined above) is inserted.

Even more preferably, the spacer is a $C_{1-20}$ alkyl being bound to $R^2$ and which $C_{1-20}$ alkyl is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl, provided that the spacer does not contain a nitrogen atom being in β- or γ-position to the amino group containing the hydrogen marked with the asterisk in formula (I).

According to another embodiment of the present invention, it is preferred that $L^2$ has a molecular weight in the range of from 14 g/mol to 750 g/mol.

Preferably, $L^2$ is attached to Z via a terminal group selected from

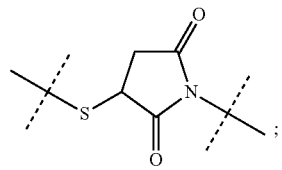

and

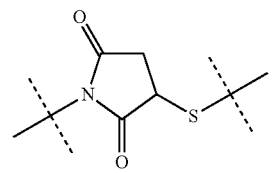

or —CO—NH—, most preferred —CO—NH—.

In case $L^2$ has such terminal group it is furthermore preferred that $L^2$ has a molecular weight in the range of from 14 g/mol to 500 g/mol calculated without such terminal group.

In another embodiment of the present invention, the spacer is preferably a $C_{1-20}$ alkyl being bound to $R^2$ and which $C_{1-20}$ alkyl is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl, provided that the spacer does not contain a nitrogen atom being in β- or γ-position to the nitrogen atom bound to the hydrogen marked with the asterisk in formula (I) and $L^2$ is attached to Z via a terminal group selected from

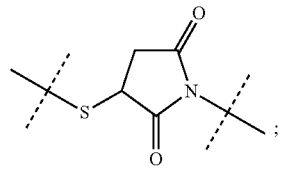

and

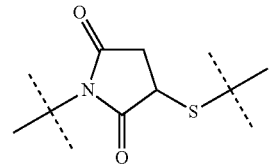

or —CO—NH—, most preferred —CO—NH—, whereby $L^2$ has a molecular weight in the range of from 14 g/mol to 500 g/mol calculated without said terminal group.

In one embodiment of the present invention, the non-biologically active linker L of the drug linker conjugate D-L may be optionally substituted further by one or more substituents. The substitution may occur at the moiety $L^1$ and/or the moiety $L^2$ including the respective preferred definitions of $L^1$ and/or $L^2$. In general, any substituent may be used as far as the cleavage principle is not affected.

Preferably, one or more further optional substituents are independently selected from the group consisting of halogen; CN; COOR$^9$; OR$^9$; C(O)R$^9$; C(O)N(R$^9$R$^{9a}$); S(O)$_2$N (R$^9$R$^{9a}$); S(O)N(R$^9$R$^{9a}$); S(O)$_2$R$^9$; S(O)R$^9$; N(R$^9$)S(O)$_2$N (R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C (O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{1a}$)—; and —OC(O)N(R$^{11}$R$^{11a}$);

R$^9$, R$^{9a}$, R$^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N (R$^{11a}$)—; —S—; —N(R$^{11}$)—; —OC(O)R$^{11}$; —N(R$^{11}$)C (O)—; —N(R$^{11}$)S(O)$_2$—; —N(R$^{11}$)S(O)—; —N(R$^{11}$)C(O) O—; —N(R$^{11}$)C(O)N(R$^{1a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$ R$^{12}$; S(O)R$^{12}$; N(R$^{12}$)S(O)$_2$N(R$^{12a}$R$^{12}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N (R$^{12a}$R$^{12b}$); OC(O)N(R$^{12}$R$^{12a}$); or $C_{1-6}$ alkyl, wherein $C_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or $C_{1-6}$ alkyl, wherein $C_{1-6}$ alkyl is optionally substituted with one or more halogen, which are the same or different.

The carrier group Z is bound to the moiety $L^2$. In case the moiety $L^2$ is a chemical bond, the carrier group Z is directly bound to the moiety $L^1$ without a spacer in-between. For the sake of completeness, it is indicated that in case L contains more than one $L^2$ moieties and by consequence more than one carrier group Z. The respective carrier groups Z may be selected independently from each other and independently from the definition of $L^2$. For example, in case of two $L^2$ moieties, one carrier group Z can be directly bound to $L^1$ ($L^2$ is a chemical bond) and the second (different) carrier group Z can be bound to $L^1$ by a spacer ($L^2$). The carrier group Z can be any carrier group known to a person skilled in the art.

Suitable carriers are polymers or $C_{8-18}$ alkyl groups.

Preferably, the carrier group Z is a polymer, more preferably a polymer with a molecular weight ≥500 g/mol.

The term polymer describes a molecule comprised of repeating structural units connected by chemical bonds in a linear, circular, branched, crosslinked or dendrimeric way or a combination thereof, which can be of synthetic or biological origin or a combination of both.

Preferred polymers are selected from 2-methacryloyl-oxyethyl phosphoyl cholins, hydrogels, PEG-based hydrogels, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly (cyanoacrylates), poly(dimethylacrylamides), poly(esters), poly(ethylenes), poly(ethyleneglycols), poly(ethylene oxides), poly(ethyl phosphates), poly(ethyloxazolines), poly (glycolic acids), poly(hydroxyethyl acrylates), poly(hydroxyethyloxazolines), poly(hydroxymethacrylates), poly (hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

As indicated above, the carrier group Z may be a hydrogel (as one option for a polymer). Hydrogels to be used are known in the art. Suitable hydrogels may be used which are described in WO-A 2006/003014 or EP-A 1 625 856. Accordingly, a hydrogel may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allow them to swell in aqueous media. The chains of the network are connected in such a fashion that pores exist and that a substantial fraction of these pores are of dimensions between 1 nm and 1000 nm.

In a preferred embodiment of the present invention, the carrier group Z is a biodegradable polyethylene glycol based water-insoluble hydrogel comprising backbone moieties which are linked together by hydrolytically degradable bonds. In one embodiment the water-insoluble hydrogel is further characterized in that the time period for the complete degradation of the hydrogel by hydrolysis of the degradable bonds into water-soluble degradation products comprising one or more backbone moieties is twice or less than the time period for the release of the first 10 mol-% of backbone moieties based on the total amount of backbone moieties in the hydrogel.

The hydrolytically degradable bonds of said hydrogels preferably are ester bonds. The backbone moieties can be linked together by crosslinkers.

Preferably, the covalent attachment formed between the linker and the carrier is a permanent bond and the carrier is a hydrogel.

Preferably, the carrier is a biodegradable polyethylene glycol (PEG) based water-insoluble hydrogel. The term "PEG based" as understood herein means that the mass proportion of PEG chains in the hydrogel is at least 10% by weight, preferably at least 25%, based on the total weight of the hydrogel. The remainder can be made up of other spacers and/or oligomers or polymers, such as oligo- or polylysines.

Moreover the term "water-insoluble" refers to a swellable three-dimensionally crosslinked molecular network froming the hydrogel. The hydrogel if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

Another aspect of the present invention is a carrier-linked prodrug comprising a biodegradable hydrogel of the present invention as carrier, wherein a number of permanent linkages of the backbone moieties exist with a transient prodrug linker to which a biologically active moiety is covalently attached.

The reactive functional groups of a reactive biodegradable hydrogel or modified reactive biodegradable hydrogel serve as attachment points for direct linkage through the before mentioned permanent linkages of drug-linker conjugate. Ideally, the hydrogel-connected drug-linker conjugates are dispersed homogeneously throughout the hydrogel according to the invention, and may or may not be present on the surface of the hydrogel according to the invention.

The functional groups may be attached to a linear chain. In this case, the functional groups may be spaced regularly or irregularly across the chain, or alternatively, the chain may be terminated by two dendritic moieties, providing for the total of functional groups.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide.

According to this invention, the biodegradable hydrogel according to the invention is composed of backbone moieties interconnected by hydrolytically degradable bonds.

In a hydrogel carrying drug-linker conjugates according to the invention, a backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the degradation kinetics of the hydrogel according to the invention.

In a hydrogel according to the invention, a backbone moiety is characterized by a number of functional groups, consisting of interconnected biodegradable and reactive functional groups. Preferably, the sum of interconnected biodegradable and reactive functional groups is 16-128, preferred 20-100, more preferred 24-80 and most preferred 30-60.

The functional groups may be attached to a linear chain. In this case, the functional groups may be spaced regularly or irregularly across the chain, or alternatively, the chain may be terminated by two dendritic moieties, providing for the total of functional groups.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithine, diaminobutyric acid, trilysine, tetralysine, pentalysine, hexylysine, heptalysine, octalysine, nonalysine, decalysine, undecalysine, dodecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly (ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferentially, a backbone moiety is characterized by having a branching core, from which at least three chains extend. Such branching cores may be provided by suitably substituted derivatives of poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be provided by suitably substituted derivatives of poly- or oligoamines such as trilysine, tetralysine, pentalysine, hexylysine, heptalysine, octalysine, nonalysine, decalysine, undecalysine, dedecalysine, tridecalysine, tetradecalysine, pentadecalysine or oligolysines, polyethyleneimines, polyvinylamines. Preferably, the branching core extends three to sixteen chains, more preferably four to eight. Preferably, such chain is a linear polyethylene glycol chain, of which one end is connected to the branching core and the other to a hyperbranched dendritic moiety.

Preferably, a PEG-based polymeric chain is a suitably substituted polyethylene glycol derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 1 kDa to 15 kDa and even more preferably 1 kDa to 10 kDa.

It is understood that the terminal amine groups of the above mentioned multi-arm molecules are present in bound form in the backbone moiety to provide further interconnected functional groups and reactive functional groups of a backbone moiety.

Preferred branching cores may be provided by suitably substituted derivatives of pentaerythritol, trilysine, tetralysine, pentalysine, hexylysine, heptalysine or oligolysine, low-molecular weight PEI, hexaglycerine, tripentaerythritol. Preferably, a chain is a suitably substituted polyethylene glycol derivative (PEG based).

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Preferably, the sum of interconnecting biodegradable linkages and permanent linkages connecting backbone moieties to prodrug-linker and blocking groups is equally divided by the number of chains extending from the branching core. For instance, if there are 32 interconnected and biodegradable and permanent linkages, eight linkages may be provided by each of the four chains extending from the core, preferably by means of dendritic moieties attached to the terminus of each chain. Alternatively, four linkages may be provided by each of eight chains extending from the core or two groups by each of sixteen chains.

The sum of interconnected and reactive functional groups of a backbone moiety is equally divided by the number of chains extending from the branching core. If the number of chains extending from the branching core does not allow for an equal distribution, it is preferred that the deviation from the mean number of the sum of interconnected and reactive functional groups per chain is kept to a minimum.

More preferably, the sum of interconnected and reactive functional groups of a backbone moiety is equally divided by the number of chains extending from the branching core. For instance, if there are 32 interconnected and reactive functional groups, eight groups may be provided by each of the four chains extending from the core, preferably by means of dendritic moieties attached to the terminus of each chain. Alternatively, four groups may be provided by each of eight chains extending from the core or two groups by each of sixteen chains.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties are comprised of trilysine, tetralysine, pentalysine, hexylysine, heptalysine in bound form, most preferred trilysine, pentalysine or heptalysine, ornithine, diaminobutyric acid in bound form.

Preferred structures for corresponding chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 2.5 kDa to 15 kDa and even more preferably 5 kDa to 10 kDa.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 functional groups, and at most 63 branchings and 64 functional groups, preferred at least 7 branchings and at least 8 reactive functional groups and at most 31 branchings and 32 functional groups.

Examples for such dendritic moieties are lysine, dilysine, trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine.

Also such multi-arm PEG derivatives may be connected to dendritic moieties. Preferably, each dendritic moiety has a molecular weight in the range of from 0.4 kDa to 2 kDa. Examples for such dendritic moieties are lysine, dilysine, trilysine, tetralysine, pentalysine, hexylysine, heptalysine, most preferred trilysine, pentalysine or heptalysine.

Most preferably, the hydrogel carrier of the present invention is characterized in that the backbone moiety has a quarternary carbon of formula C(A-Hyp)4, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected functional groups and reactive functional groups.

Preferably, each A is independently selected from the formula —(CH2)n1(OCH2CH2)nX—, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide comprises lysine in bound form. Preferably, each dendritic moiety Hyp has a molecular weight in the range of from 0.4 kDa to 4 kDa. It is understood that a backbone moiety C(A-Hyp)4 can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of polyethyleneglycol based crosslinker reagents results in a permanent amide bond.

Preferably, C(A-Hyp)4 has a molecular weight in the range of from 1 kDa to 20 kDa, more preferably 1 kDa to 15 kDa and even more preferably 1 kDa to 10 kDa.

One preferred backbone moiety is shown below, dashed lines indicate interconnecting biodegradable linkages to crosslinker moieties and n is an integer of from 5 to 50: backbone moiety has a quarternary carbon of formula C(A-Hyp)4, wherein each A is independently a polyethyleneglycol based polymeric chain terminally attached to the quarternary carbon by a permanent covalent bond and the distal end of the polymeric chain is covalently bound to a dendritic moiety Hyp, each dendritic moiety Hyp having at least four linkages representing the interconnected and biodegradable and permanent linkages. Each backbone moiety contains at least 16 interconnected and biodegradable and permanent linkages, preferably 20 to 64 and more preferably 28 to 64 linkages.

Preferably, each A is independently selected from the formula —(CH2)n1(OCH2CH2)nX—, wherein n1 is 1 or 2; n is an integer in the range of from 5 to 50; and X is a functional group covalently linking A and Hyp.

Preferably, A and Hyp are covalently linked by an amide functional group.

Preferably, the dendritic moiety Hyp is a hyperbranched polypeptide. Preferably, the hyperbranched polypeptide comprises lysine, most preferably Hyp is undecalysinyl. Preferably, each dendritic moiety Hyp has a molecular weight in the range of from 0.4 kDa to 4 kDa. It is understood that a backbone moiety C(A-Hyp)4 can consist of the same or different dendritic moieties Hyp and that each Hyp can be chosen independently. Each moiety Hyp consists of between 5 and 21 lysines, preferably of at least 7 lysines.

Also preferably, the hyperbranched polypeptide comprises lysine, most preferably Hyp is heptalysinyl. Preferably, each dendritic moiety Hyp has a molecular weight in the range of from 0.4 kDa to 2 kDa.

The sum of interconnecting biodegradable linkages and permanent linkages connecting backbone moieties to pro-drug-linker and blocking groups can be equally or unequally divided by the number of chains extending from the branching core.

Preferably, C(A-Hyp)4 has a molecular weight in the range of from 1 kDa to 20 kDa, more preferably 1 kDa to 15 kDa and even more preferably 1 kDa to 10 kDa.

Preferably, L2 is attached to Z through a thiosuccinimide group or amide group, preferably an amide group, which in turn is attached to the hydrogel's backbone moiety through a spacer, such as an oligoethylene glycol chain. Preferably, the linkage of this spacer chain to the backbone moiety is a permanent bond, preferably an amide bond.

Biodegradability of the hydrogels according to the present invention is achieved by introduction of hydrolytically degradable bonds.

The terms "hydrolytically degradable", "biodegradable" or "hydrolytically cleavable", "auto-cleavable", or "self-cleavage", "self-cleavable", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like.

If present in a hydrogel according to the invention as degradable interconnected functional group, preferred biodegradable linkages are esters, carbonates, phosphoesters and sulfonic acid esters and most preferred are esters or carbonates.

The term "hydrolytically degradable" refers within the context of the present invention to linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates. It is understood that for in vitro studies accelerated conditions like, for example, pH 9, 37° C., aqueous buffer, may be used for practical purposes.

Permanent linkages are non-enzymatically hydrolytically degradable under physiological conditions (aqueous buffer at pH 7.4, 37° C.) with half-lives of six months or longer, such as, for example, amides.

The degradation of the hydrogel is a multi-step reaction where a multitude of degradable bonds is cleaved resulting in degradation products which may be water-soluble or water-insoluble. However each water-insoluble degradation product further comprises degradable bonds so that it can be cleaved in that water-soluble degradation products are obtained. These water-soluble degradation products may comprise one or more backbone moieties. It is understood that released backbone moieties may, for instance, be permanently linked to spacer or blocking groups and/or prodrug-linker degradation products.

The total amount of backbone moieties can be measured in solution after complete degradation of the hydrogel, and during degradation, fractions of soluble backbone degradation products can be separated from the insoluble hydrogel and can be quantified without interference from other soluble degradation products released from the hydrogel. A hydrogel object may be separated from excess water of buffer of physiological osmolality by sedimentation or centrifugation. Centrifugation may be performed in such way that the supernatant provides for at least 10% of the volume of the swollen hydrogel. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods. For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

In such hydrogel-linked prodrugs according to the invention, it is desirable that almost all drug release (>90%) has occurred before a significant amount of release of the backbone degradation products (<10%) has taken place. This can be achieved by adjusting the hydrogel-linked prodrug's half-life versus the hydrogel degradation kinetics.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by an interconnected functional groups.

Alternatively, backbone moieties may be linked together through crosslinker moieties, each crosslinker moiety is terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Preferably, the biodegradable hydrogel carrier is composed of backbone moieties interconnected by hydrolytically degradable bonds and the backbone moieties are linked together through crosslinker moieties.

The biodegradable hydrogel carrier may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

If present in a hydrogel according to the invention as degradable interconnected functional group, preferred biodegradable linkages are carboxylic esters, carbonates, phosphoesters and sulfonic acid esters and most preferred are carboxylic esters or carbonates.

Preferably, crosslinker moieties have a molecular weight in the range of from 60 Da to 5 kDa, more preferably, from 0.5 kDa to 4 kDa, even more preferably from 1 kDa to 4 kDa, even more preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the formation of a biodegradable hydrogel according to the invention.

Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are poly(lactic acid) or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

Preferably, the hydrogel earner is composed of backbone moieties interconnected by hydrolytically degradable bonds.

Preferably, backbone moieties may be linked together through crosslinker moieties, each crosslinker moiety being terminated by at least two of the hydrolytically degradable bonds. In addition to the terminating degradable bonds, the crosslinker moieties may contain further biodegradable bonds. Thus, each end of the crosslinker moiety linked to a backbone moiety shows a hydrolytically degradable bond, and additional biodegradable bonds may optionally be present in the crosslinker moiety.

The hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds. The term biodegradable bond describes linkages that are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates.

In one embodiment, a crosslinker moiety consists of a polymer. Preferably, crosslinker moieties have a molecular weight in the range of from 60 Da to 5 kDa, more preferably, from 60 Da to 4 kDa, even more preferably from 60 Da to 3 kDa.

Also preferably, crosslinker moieties have a molecular weight in the range of from 0.5 kDa to 5 kDa, more preferably, from 1 kDa to 4 kDa, even more preferably from 1 kDa to 3 kDa.

In addition to oligomeric or polymeric crosslinking moieties, low-molecular weight crosslinking moieties may be used, especially when hydrophilic high-molecular weight backbone moieties are used for the hydrogel formation.

Preferably, the polyethyleneglycol based crosslinker moieties are hydrocarbon chains comprising ethylene glycol units, optionally comprising further functional groups, wherein the polyethyleneglycol based crosslinker moieties comprise at least each methylene glycol units, wherein m is an integer in the range of from 1 to 70. Preferably, the polyethyleneglycol based crosslinker moieties have a molecular weight in the range of from 60 Da to 5 kDa. Also preferably, m is an integer in the range of from 10 to 70. Preferably, the polyethyleneglycol based crosslinker moieties have a molecular weight in the range of from 0.5 kDa to 5 kDa.

Preferably, the crosslinker moieties are PEG-based, preferably represented by only one PEG-based molecular chain. Preferably, the polyethyleneglycol-based crosslinkers are hydrocarbon chains comprising one or more ethylene glycol units, optionally comprising further functional groups, wherein the polyethyleneglycol based crosslinker moieties comprise at least each methylene glycol units, wherein m is an integer in the range of from 1 to 70. Preferably, the polyethyleneglycol based crosslinkers have a molecular weight in the range of from 60 Da to 5 kDa.

In one embodiment, monomers constituting the polymeric crosslinker moieties are connected by biodegradable bonds. Such polymeric crosslinkers may contain up to 100 biodegradable bonds or more, depending on the molecular weight of the crosslinker moiety and the molecular weight of the monomer units. Examples for such crosslinkers are polylactic acid or polyglycolic acid based.

Also preferably, the crosslinker moieties are PEG based, preferably represented by only one PEG based molecular chain. Preferably, the polyethyleneglycol based crosslinkers are hydrocarbon chains comprising ethylene glycol units, optionally comprising further functional groups, wherein the polyethyleneglycol based crosslinker moieties comprise at least each methylene glycol units, wherein m is an integer in the range of from 10 to 70. Preferably, the polyethyleneglycol based crosslinkers have a molecular weight in the range of from 0.5 kDa to 5 kDa.

In a preferred embodiment of the present invention the crosslinker moiety consists of a PEG chain, which is symmetrically connected through ester bonds to two alpha, omega-aliphatic dicarboxylic spacers provided by backbone moieties through permanent amide bonds. The dicarboxylic acids consists of 3 to 12 carbon atoms, most preferably between 5 and 8 carbon atoms and may be substituted at one or more carbon atom. Preferred substituents are alkyl groups, hydroxy groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

the hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel carrier according to the invention.

The degradation of the biodegradable hydrogel carrier according to the invention is a multi-step reaction where a multitude of degradable bonds is cleaved resulting in degradation products which may be water-soluble or water-insoluble. However, water-insoluble degradation products may further comprise degradable bonds so that they can be cleaved in that water-soluble degradation products are obtained. These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the hydrogel carriers of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object according to the invention may be separated from excess water of buffer of physiological osmolality by sedimentation or centrifugation. Centrifugation may be performed in such way that the supernatant provides for at least 10% of the volume of the swollen hydrogel according to the invention. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Preferably, water-soluble degradation products may be separated from water-insoluble degradation products by filtration through 0.45 µm filters, after which the water-soluble degradation products can be found in the flow-through. Water-soluble degradation products may also be separated from water-insoluble degradation products by a combination of a centrifugation and a filtration step.

For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

In such hydrogel-linked prodrugs according to the invention, it is desirable that almost all drug release (>90%) has occurred before a significant amount of release of the backbone degradation products (<10%) has taken place. This can be achieved by adjusting the hydrogel-linked prodrug's half-life versus the hydrogel degradation kinetics.

The hydrogel-linked prodrug of the present invention can be prepared starting from the hydrogel of the present invention by convenient methods known in the art. It is clear to a practitioner in the art that several routes exist. For example the prodrug linker mentioned above to which the biologically active moiety is covalently attached can be reacted with the reactive functional groups of the hydrogel of the present invention with or with already bearing the active moiety in part or as whole.

In a preferable method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homomultifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha,beta unsaturated Michael acceptors like vinylsulfone, thiol, hydroxyl groups.

If the crosslinker reagent reactive functional groups are used substoichiometrically with respect to backbone reactive functional groups, the resulting hydrogel will be a reactive hydrogel with free reactive functional groups attached to the backbone structure.

Optionally, the linker may be first conjugated to the drug compound and the resulting prodrug linker conjugate may then react with the hydrogel's reactive functional groups. Alternatively, after activation of one of the functional groups of the linker, the linker-hydrogel conjugate may be contacted with drug compound in the second reaction step and excess drug may be removed by filtration after conjugation of the drug to the hydrogel-bound linker.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably fom 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or five lysines would be attached to each arm of a 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

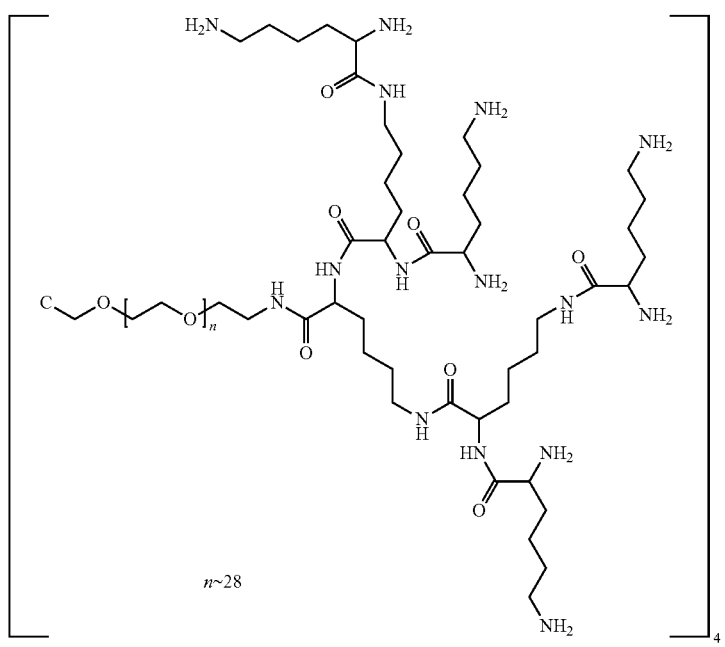

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, most adipic acid or glutaric acid. Preferred protecting group for half ester formation is the benzylic group. The resulting bis dicarboxylic acid PEG half esters are converted into more reactive carboxy compounds such as acyl chlorides or active esters, eg pentafluorophenyl or N-hydroxysuccinimide esters, most preferred N-hydroxysuccinimde esters, of which preferred selected structure is shown below.

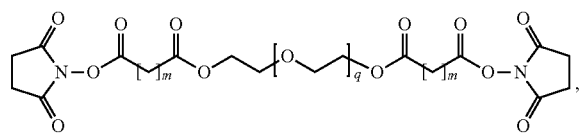

wherein each m independently is an integer ranging from 2 to 4, and q is an integer of from 3 to 100.

More preferred is the following structure:

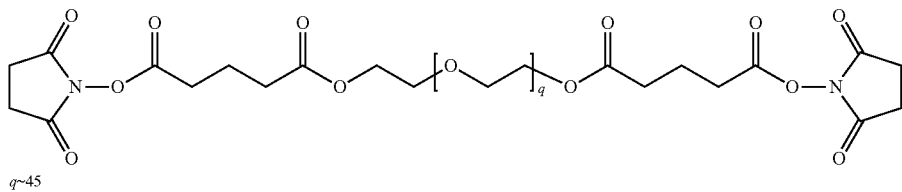

$q\sim 45$

Alternatively, the bis dicarboxylic acid PEG half esters may be activated in the presence of a coupling agent such as DCC or HOBt or PyBOP.

In an alternative embodiment the backbone reagent carries carboxyl groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker polymerizable groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylethylenene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

In an alternative embodiment of this invention, multi-functional moieties are coupled to the reactive functional groups of the polymerized reactive hydrogel to increase the number of functional groups which allows to increase the drug load of the hydrogel. Such multi-functional moieties may be pro vided by suitably substituted derivatives of lysine, dilysine, trilysine, tetralysine, pentalysine, hexylysine, heptalysine, or oligolysine, low-molecular weight PEI. Preferably, the multifunctional moiety is lysine.

Further, such hydrogel according to the invention may be functionalized with a spacer carrying the same functional group, for instance, amino groups may be introduced into the hydrogel by coupling a heterobifunctional spacer, such as suitably activated COOH-(EG)$_6$-NH-fmoc (EG=ethylene glycol), and removing the fmoc-protecting group.

In yet another embodiment, a drug compound is first conjugated to a linker in such a fashion that the linkage between drug compound and linker is a covalent transient linkage such as an aromatic amide linkage, and is subsequently reacted with a reactive biodegradable hydrogel to form a prodrug according to the invention.

Further, such hydrogel according to the invention may be functionalized with a spacer carrying a different reactive functional group than provided by the hydrogel. For instance, maleimide reactive functional groups may be introduced into the hydrogel by coupling a suitable heterobifunctional spacer such as Mal-(EG)$_6$-NHS to the hydrogel. Such functionalized hydrogel can be further conjugated to drug-linker reagents, carrying a reactive thiol group on the linker moiety to form carrier-linked prodrugs according to the present invention.

After loading the drug-linker conjugate to the functionalized maleimido group-containing hydrogel, all remaining functional groups are capped with a suitable blocking reagents, such as mercaptoethanol, to prevent undesired side-reactions.

A particularly preferred method for the preparation of a prodrug of the present invention comprises the steps of (a) reacting a compound of formula C(A'-X$^1$)$_4$, wherein A'-X$^1$ represents A before its binding to Hyp or a precursor of Hyp and X$^1$ is a suitable chemical functional group, with a compound of formula Hyp'-X$^2$, wherein Hyp'-X$^2$ represents Hyp before its binding to A or a precursor of Hyp and X$^2$ is a suitable chemical functional group to react with X$^1$;

(b) optionally reacting the resulting compound from step (a) in one or more further steps to yield a compound of formula C(A-Hyp)$_4$ having at least four chemical functional groups;

(c) reacting the at least four chemical functional groups of the resulting compound from step (b) with a poly(ethylene glycol) based crosslinker precursor reagent, wherein the crosslinker precursor reagent is used in a sub-stoichiometric amount compared to the total number of functional groups of C(A-Hyp)$_4$ to yield a hydrogel according to the invention;

(d) reacting remaining un-reacted reactive functional groups (representing the reactive functional groups of the backbone comprised in the reactive biodegradable hydrogel of the present invention) in the hydrogel backbone of step (c) with a covalent conjugate of biologically active moiety and transient prodrug linker or first reacting the un-reacted reactive functional groups with the transient prodrug linker and subsequently with the biologically active moiety;

(e) optionally capping remaining un-reacted reactive functional groups to yield a prodrug of the present invention.

Specifically, hydrogels of the present invention are synthesized as follows:

For bulk polymerization, backbone reagent and crosslinker reagent are mixed in a ratio amine/active ester of 2:1 to 1.05:1. Both backbone reagent and crosslinker reagent are dissolved in DMSO to give a solution with a concentration of 5 to 50 g per 100 mL, preferably 7.5 to 20 g per 100 ml and most preferably 10 to 20 g per 100 ml.

To effect polymerization, 2 to 10% (vol.) N,N,N',N'-tertramethylethylene diamine (TMEDA) are added to the DMSO solution containing crosslinker reagent and backbone reagent and the mixture is shaken for 1 to 20 sec and left standing. The mixture solidifies within less than 1 min.

Such hydrogel according to the invention is preferably comminuted by mechanical processes such as stirring, crushing, cutting pressing, or milling, and optionally sieving.

For emulsion polymerization, the reaction mixture is comprised of the dispersed phase and the continuous phase.

For the dispersed phase, backbone reagent and crosslinker reagent are mixed in a ratio amine/active ester of 2:1 to 1.05:1 and are dissolved in DMSO to give a to give a solution with a concentration of 5 to 50 g per 100 mL, preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly (hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Rühr- and Mischtechnik GmbH, Germany)), most preferably similar to Isojet with a diameter of 50 to 90% of the reactor diameter. Preferably, stirring is initated before addition of the dispersed phase. Stirrer speed is set to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N, N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 μm and a 32 μm deck to give hydrogel microparticles according to the invention.

The hydrogel for the prodrug of the present invention can be obtained from the preparation methods in form of microparticles. In a preferred embodiment of the invention, the reactive hydrogel is a shaped article such as a mesh or a stent. Most preferably, the hydrogel is formed into microparticulate beads which can be administered as subcutaneous or intramuscular injectably by means of a standard syringe. Such soft beads may have a diameter of between 1 and 500 micrometer.

Preferably, such beaded hydrogel prodrugs have a diameter of between 10 and 100 micrometer if suspended in an isotonic aqueous formulation buffer, most preferably a diameter of between 20 and 100 micrometer, most preferably a diameter of between 25 and 80 micrometer.

Preferably, such beaded biodegradable hydrogel prodrugs can be administered by injection through a needle smaller than 0.6 mm inner diameter, preferably through a needle smaller than 0.3 mm inner diameter, more preferably through a needle small than 0.25 mm inner diameter, even more preferably through a needle smaller than 0.2 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the biodegradable hydrogel according to the invention swollen in a liquid at a certain concentration (w/v) and at a certain temperature, a needle of a given inner diameter connected to the outlet of such syringe, and the time required to extrude a certain volume of the biodegradable hydrogel carrier according to the invention from the syringe through the needle.

In order to provide for injectability, a volume of 1 mL of the prodrugs according to the invention swollen in water to a concentration of at least 5% (w/v) and contained in a syringe holding a plunger of a diameter of 4.7 mm can be extruded at room temperature within 10 seconds by applying a force of less than 50 Newton.

Preferably injectability is achieved for a hydrogel prodrug according to the invention swollen in water to a concentration of ca. 10% (w/v).

Within one embodiment of the present invention, in case $X^1$ is a cyclic fragment and $X^2$ is $C(R^3R^{3a})$, the order of $X^1$ (the $X^1$ fragment) and $X^2$ (the $X^2$ fragment) within the moiety $L^1$ may be changed. This means that in such a case the moiety $L^1$ is represented by formula (Ia),

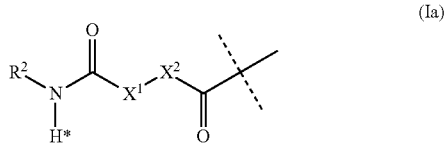
(Ia)

wherein (besides $X^1$ and $X^2$) all substituents (such as $R^2$) and fragments (such as $L^2$) have the same (chemical) definitions as indicated within the context of the present invention for formula (I).

The drug linker conjugate D-L is any combination of the aromatic amine containing biologically active moiety D and the non-biologically active linker (both) as defined above, wherein the dashed line indicates the attachment of $L^1$ to an aromatic amino group of D by forming an amide bond.

Another subject of the present invention is a method for the synthesis of a prodrug or a pharmaceutically acceptable salt thereof as defined above. Prodrugs or precursors of prodrugs according to the present invention may be prepared by known methods or in accordance with the reaction sequences described below. The starting materials used in the preparation (synthesis) of prodrugs of the invention or precursors thereof are known or commercially available, or can be prepared by known methods or as described below.

All reactions for the synthesis of the prodrugs according to the present invention including precursors such as the moiety $L^1$ according to the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the prodrugs or precursors can be purified by customary purification procedures, for example by recrystallization or chromatography.

The prodrugs according to the present invention (or a pharmaceutically acceptable salt thereof) may be prepared by a method comprising the step of reacting a prodrug precursor L-Y with a biologically active drug D-H to obtain the drug linker conjugate D-L by forming an amide bond, wherein Y is a leaving group.

In respect of the prodrug precursor L-Y, L has the same meaning as indicated above in connection with the drug linker conjugate D-L. The same holds true for the analogous employment of the prodrug precursor $L^1$-Y in respect of the moiety $L^1$ represented by formula (I) or formula (Ia), respectively.

Y is a leaving group. Such leaving groups are known to a person skilled in the art. Preferably, Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

In case the synthesis of a prodrug according to the present invention is carried out by employing a precursor $L^1$-Y, a drug linker intermediate ($L^1$-D) is obtained by reacting $L^1$-Y with the biologically active drug D-H (by forming an amide bond). In such a case, said drug linker intermediate $L^1$-D is reacted further to obtain the drug linker conjugate D-L by adding the moiety $L^2$ and the carrier group Z to said drug linker intermediate $L^1$-D. It has to be indicated that the addition of $L^2$ and/or Z to $L^1$-D may be performed in several steps by preparing further intermediate compounds prior to obtaining the drug linker conjugate D-L.

Alternatively, a prodrug precursor L*-Y may be employed instead of $L^1$-Y, wherein L* is selected from a fragment of $L^1$, $L^1$ containing at least one protecting group or $L^1$ additionally containing precursors of $L^2$ and/or Z.

Another subject of the present invention is the use of prodrugs (or a pharmaceutically acceptable salt thereof) comprising a drug linker conjugate D-L as pharmaceuticals or medicaments, respectively. With respect of the definitions of the drug linker conjugate D-L (as well as further substituents such as $L^1$ or $X^1$) the same explanations as laid out above in the context of the prodrug as such apply.

Another subject of the present invention is a pharmaceutical composition comprising an effective dose of at least one prodrug (or a pharmaceutically acceptable salt thereof) as defined above and a pharmaceutically acceptable excipient.

Furthermore, the present invention also comprises the use of such pharmaceutical compositions as pharmaceuticals or medicaments, respectively.

Examples of diseases, which can be treated by employing the prodrugs and/or the pharmaceutical compositions according to the present invention are dopamine receptor related diseases, including Parkinson's disease, neurological disorders, amyotrophic lateral sclerosis, compulsive behavior, bipolar disorders, Tourette's syndrome, depressive disorders, treatment resistant depression, fibromyalia or restless leg syndrome (RLS).

Preferred diseases to be treated are Parkinson's disease and RLS.

The use of the prodrugs and/or the pharmaceutical compositions according to the present invention includes the prophylaxis and/or treatment of said diseases. The present invention also includes a method for producing a medicament for the prophylaxis and/or treatment of said diseases. The present invention also includes a method of treating, controlling, delaying or preventing in a mammalian patient in need of the treatment of one or more conditions comprising administering to said patient a therapeutically effective amount of a prodrug (or a pharmaceutically acceptable salt thereof) according to the present invention or a respective pharmaceutical composition.

All prodrugs according to the present invention or the respective pharmaceutical compositions can be administered to animals, preferably to mammals, and in particular to humans. The prodrugs and/or pharmaceutical compositions can be administered as such or in mixtures with one another or in mixtures with other pharmaceuticals. The prodrugs and/or the respective pharmaceutical compositions according to the present invention are administered in effective doses, which are known to a person skilled in the art.

The following examples illustrate the invention without limitation.

EXAMPLES

Materials and Methods

2-Chlorotrityl chloride resin and Sieber amide resin were obtained from Merck Biosciences GmbH, Schwalbach/Ts, Germany. Boc-Gly-OH and Fmoc-Gly-OH were obtained from Merck KGaA, Darmstadt, Germany. Mal-dPEG$_6$-NHS-ester was obtained from celares GmbH, Berlin, Germany. Pramipexole dihydrochloride was optained from Carbone Scientific Co., Ltd., Wuhan, China.

All other chemicals were obtained from Sigma-ALDRICH Chemie GmbH, Taufkirchen, Germany.

Solid phase synthesis was performed on 2-Chlorotrityl chloride resin with a loading of 1.1 mmol/g or Sieber amide resin with a loading of 0.64 mmol/g. Syringes equipped with polypropylene frits were used as reaction vessels.

Loading of the first amino acid to resins was performed according to manufacturer's instructions.

Fmoc Deprotection:

For Fmoc protecting-group removal, the resin was agitated with 2/2/96 (v/v/v) piperidine/DBU/DMF (two times, 10 min each) and washed with DMF (ten times).

Standard Coupling Conditions for Acids:

Coupling of acids (aliphatic acids, Fmoc-amino acids) to free amino groups on resin was achieved by agitating resin with 2 eq of acid, 2 eq PyBOP and 4 eq DIEA in relation to free amino groups on resin (calculated based on theoretical loading of the resin) in DMF at room temperature. After 1 hour resin was washed with DMF (10 times).

3-Maleimido Propionic Acid Coupling:

Coupling of 3-maleimido propionic acid to free amino groups on resin was achieved by agitating resin with 2 eq of acid, 2 eq DIC and 2 eq HOBt in relation to free amino groups in DMF at room temperature. After 30 min, the resin was washed with DMF (10 times).

Standard Protocol for the Synthesis of Ureas on Resin:

Synthesis of ureas on resin was achieved by agitating resin with 2.5 eq of bis(pentafluorophenyl) carbonate and 5 eq DIEA in relation to free amino groups in DCM at room temperature. After 45 min resin was washed with DMF (10 times). 1 eq of amine and 2.5 eq DIEA were dissolved in DCM. Mixture was added to resin and agitated for 75 min at room temperature. Resin was washed with DMF (10 times).

Cleavage Protocol for Sieber Amide Resin:

Upon completed synthesis, the resin was washed with DCM (10 times), dried in vacuo and treated repeatedly (three times a 15 minutes) with 96/2/2 (v/v/v) DCM/TES/TFA. Eluates were combined, volatiles were removed under a nitrogen stream and product was purified by RP-HPLC. HPLC fractions containing product were combined and lyophilized.

Cleavage Protocol for 2-chlorotrityl Chloride Resin:

Upon completed synthesis, the resin was washed with DCM, dried in vacuo and treated three times for 30 minutes with 7/3 (v/v) DCM/HFIP. Eluates were combined, volatiles were removed under a nitrogen stream and product was purified by RP-HPLC. HPLC fractions containing product were combined and lyophilized.

RP-HPLC Purification:

RP-HPLC was done on a 100×20 or a 100×40 mm C18 ReproSil-Pur 3000DS-3 5µ column (Dr. Maisch, Ammerbuch, Germany) connected to a Waters 600 HPLC System and Waters 2487 Absorbance detector. Linear gradients of solution A (0.1% TFA in H$_2$O) and solution B (0.1% TFA in acetonitrile or 0.1% TFA in 2/1 (v/v) methanol/isopropanol) were used. HPLC fractions containing product were lyophilized.

Analytics: Ultra performance liquid chromatography-electronspray ionization mass spectrometry (UPLC-ESI-MS) was performed on a Waters Acquity Ultra Performance LC instrument connected to a Thermo scientific LTQ Orbitrap Discovery instrument and spectra were, if necessary, interpreted by Thermo scientific software xcalibur.

Mass spectra of PEG products showed a series of $(CH_2CH_2O)_n$ moieties due to polydispersity of PEG staring materials. For easier interpretation only one single representative m/z signal is given in the examples.

Example 1

Synthesis of Linker Pramipexole Conjugate (1b)

Synthesis of Intermediate (1a)

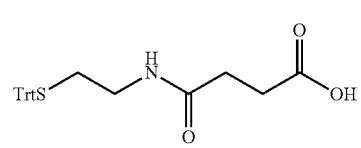

S-tritylcysteamine (100 mg, 0.313 mmol), succinic anhydride (323 mg, 3.130 mmol) and DIEA (273 µL, 1.567 mmol) were dissolved in dry DCM (2.2 mL) and agitated for 30 min at room temperature. The mixture was acidified by addition of AcOH (0.7 mL), diluted with diethyl ether and washed twice with water. The organic phase was dried over MgSO$_4$, the solvent was evaporated under reduced pressure.

Yield: 95 mg (0.226 mmol).

MS: m/z 442.1=[M+Na]$^+$ (calculated=442.5 g/mol).

Synthesis of (1b)

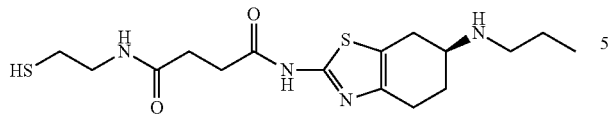

1b

Reagent 1a (30 mg, 0.072 mmol), PyBOP (45 mg, 0.086 mmol) and N-methyl morpholine (79 μL, 0.715 mmol) were dissolved in DMSO (1 mL). Pramipexole dihydrochloride (81 mg, 0.286 mmol) was added and the mixture was stirred for 16 h. The reaction was quenched by addition of acetic acid and the mixture was diluted with 3.5 mL acetonirile/water 1/1+0.1% TFA. The trityl protected intermediate of 1b was purified by RP-HPLC. After lyophilisation 21 mg (0.029 mmol) of the TFA salt were obtained.

MS: m/z 613.4=[M+H]$^+$ (calculated=613.9 g/mol).

For trityl deprotection the lyophilisate was dissolved in HFIP (2 mL), TES (20 μL) was added, and the mixture was incubated for 10 min. Volatiles were evaporated and 1b was purified by RP-HPLC.

Yield: 12 mg (0.025 mmol, TFA salt).
MS: m/z 371.2=[M+H]$^+$ (MW calculated=371.2 g/mol).

Example 2

Synthesis of Linker Pramipexole Conjugate (2b)

Synthesis of Intermediate (2a)

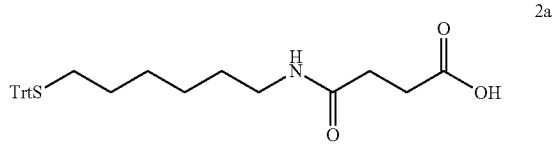

2a 2a was synthesized as described for 1a except for the use of 6-(tritylthio)hexane-1-amine instead of trityl cysteamine.

Yield: 170 mg (0.226 mmol).
MS: m/z 498.2=[M+Na]$_+$, (calculated=498.6 g/mol).

Synthesis of (2b)

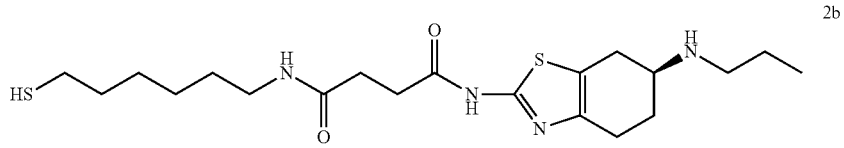 [SMILES: CCCN[C@H]1CCc2nc(NC(=O)CCC(=O)NCCCCCCS)sc2C1]

2b 2b was synthesized as described for 1b except for the use of 2a instead of 1a.

2b: Yield: 3.5 mg (0.006 mmol, TFA salt).
MS: m/z 427.2=[M+H]$^+$, (MW calculated=427.2 g/mol).

Example 3

Synthesis of Intermediate (3a)

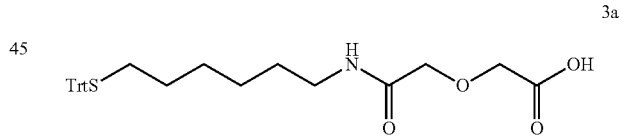

3a 3a was synthesized as described for 2a except for the use of 1,4-dioxane-2,6-dione instead of succinic anhydride.

Yield: 117 mg (0.237 mmol).
MS: m/z 983.4=[2M+H]$^+$ (calculated=984.2 g/mol).

Synthesis of Linker Pramipexole Intermediate (3b)

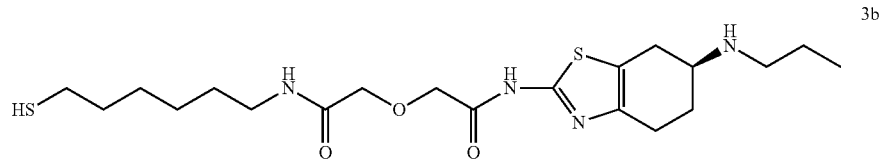 [SMILES: CCCN[C@H]1CCc2nc(NC(=O)COCC(=O)NCCCCCCS)sc2C1]

3b 3b was synthesized as described for 1b except for the use of 3a instead of 1a. The coupling of pramipexole was completed within 30 min.

3b: Yield: 4.5 mg (0.008 mmol, TFA salt).
MS: m/z 443.2=[M+H]$^+$, (calculated=443.7 g/mol).

Example 4

Synthesis of Linker Pramipexol Conjugate (4b)

Synthesis of Intermediate (4a)

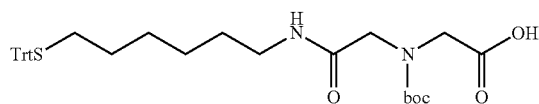
4a 4a was synthesized as described for 2a except for the use of tert-butyl 2,6-dioxomorpholine-4-carboxylate instead of succinic anhydride.

Yield: 148 mg (0.250 mmol).
MS: m/z 591.3=[M+H]$^+$, (calculated=591.8 g/mol).

Synthesis of (4b)

4b was synthesized as described for 1b except for the use of 4a instead of 1a. The coupling of pramipexole was completed within 40 min.

Prior trityl and boc deprotection 38 mg (0.042 mmol, TFA salt) of the intermediate were isolated after RP-HPLC purification and lyophilisation.

MS: m/z 784.4=[M+H]$^+$, (calculated=785.1 g/mol).

11 mg of the intermediate were used for deprotection of the thiol. For deprotection the intermediate was dissolved in 1.2 mL HFIP/TFA (1/1), 48 µL of TES/water (1/1) was added, and the solution was agitated for 1.5 h. Volatiles were removed and the product was purified by RP-HPLC.

Yield: 7.7 mg (0.011 mmol, double TFA salt).
MS: m/z 442.2=[M+H]$^+$, (calculated=442.7 g/mol).

Example 5

Synthesis of Linker Pramipexole Conjugate (5b)

Synthesis of Intermediate (5a)

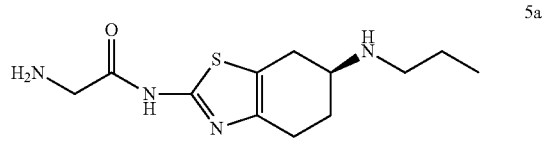 [SMILES: CCCN[C@H]1CCc2nc(NC(=O)CN)sc2C1]
5a

Boc-Gly-OH (659 mg, 3.76 mmol), PyBOP (2.35 g, 4.51 mmol) and N-methyl morpholine (4.14 mL, 37.6 mmol) were dissolved in DMSO (20 mL). Pramipexole dihydrochloride (2.14 g, 7.52 mmol) were added, and the mixture was stirred for 1 h. The solution was diluted with 300 mL 1 M NaOH solution, saturated with NaCl, and extracted with DCM (8×70 mL). The combined organic phases were dried over MgSO$_4$, the solvent was evaporated under reduced pressure, and the residue purified by RP-HPLC. After lyophilisation 721 mg (1.49 mmol, TFA salt) of the Boc protected derivative were obtained.

MS: m/z 369.2=[M+H]$^+$, (calculated=369.5 g/mol).

For deprotection the intermediate was dissolved in 3 M methanolic HCl (10 mL), concentrated aqueous HCl (400 µL) were added, and the mixture was agitated for 4 h. The solvent was removed under reduced pressure and the residue was dried in vacuo.

Yield: 490 mg (1.44 mmol, double HCl salt).
MS: m/z 269.1=[M+H]$^+$ (calculated=269.4 g/mol).

Synthesis of (5b)

1. 4-nitrophenyl chloroformate
2. 5a
3. deprotection

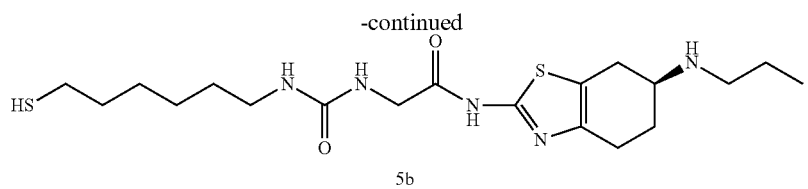

5b 6-(Tritylthio)hexane-1-amine (1.21 g, 3.22 mmol) and p-nitrophenyl chloroformate (0.78 g, 3.86 mmol) were suspended in dry THF (15 mL). DIEA (841 µL, 4.83 mmol) was added, and the resulting solution was stirred at room temperature for 2 h. After acidification by addition of acetic acid the solvent was evaporated under reduced pressure, and the residue was purified by RP-HPLC. 1.21 g (2.25 mmol) p-nitrophenyl carbamate were obtained after lyophilisation.

The carbamate (801 mg, 1.48 mmol) was dissolved in DMSO (4.4 mL) and added dropwise to a stirred solution of 5a (490 mg, 1.44 mmol) and DIEA (800 µL, 4.60 mmol) in DMSO (7 mL) within 30 min. The mixture was agitated for 4.5 h at room temperature. The solution was diluted with 0.5 M NaOH solution (300 mL) and extracted with DCM (6×70 mL). The combined organic phases were dried over MgSO$_4$, the solvent was evaporated under reduced pressure, and the conjugate was purified by RP-HPLC to obtain 254 mg (0.323 mmol, TFA salt) of the trityl protected intermediate.

MS: m/z 670.3=[M+H]$^+$ (calculated=671.0 g/mol).

For deprotection the intermediate (248 mg, 0.32 mmol) was incubated in HFIP (6 mL) and TES (240 µL) for 30 min at room temperature. Volatiles were evaporated, and the residue was purified by RP-HPLC.

Yield: 167 mg (0.31 mmol, TFA salt).

MS: m/z 428.2=[M+H]$^+$, (calculated=428.6 g/mol).

Example 6

Synthesis of (6)

6

For the synthesis of intermediate 6 glutaric acid anhydride (401 mg, 3.52 mmol), pramipexole dihydrochloride (200 mg, 0.70 mmol), and pyridine (567 µL, 7.04 mmol) were dissolved in dry DMSO (2 mL). The mixture was stirred for 18 hours. The mixture was acidified by addition of acidic acid and 6 was purified by RP-HPLC.

Yield: 191 mg (0.43 mmol, TFA salt).

MS: m/z 326.2=[M+H]$^+$, (calculated=326.4 g/mol).

Example 7

Synthesis of OEG-Carrier (7)

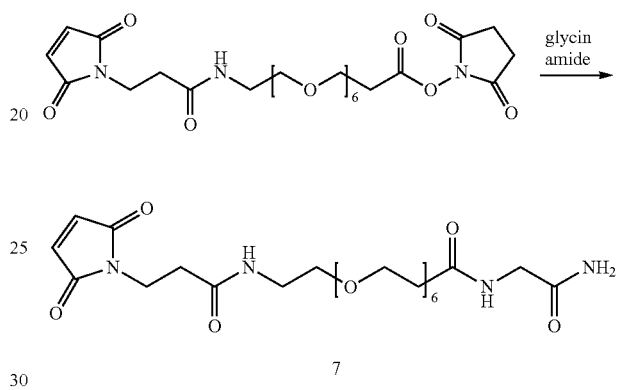

7

Maleimide-dPEG$_6$-NHS-ester (75 mg, 0.125 mmol) was dissolved in 7/3 acetonitrile/water (3 mL). 0.5 M phosphate buffer pH 7.0 (300 µL) and glycine amide hydrochloride (41 mg, 0.374 mmol) were added, and the solution was aggitated 30 min at RT. The mixture was diluted by addition of water (3 mL) and 7 purified by RP-HPLC.

Yield: 54 mg (0.096 mmol).

MS: m/z 561.3=[M+H]$^+$, (calculated=561.6 g/mol).

Example 8

Synthesis of OEG-Carrier-Resin (8)

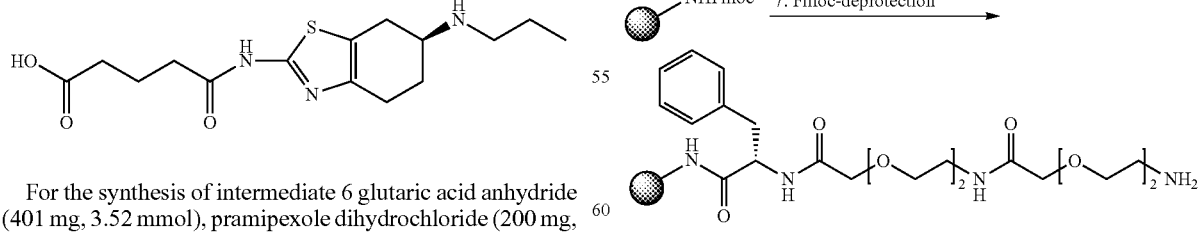

8

PEG-carrier 8 was synthesized on Sieber amide resin (600 mg, 0.38 mmol) by loading of the resin with Fmoc-Phe-OH, Fmoc-deprotection, coupling with Fmoc-8-amino-3,6-dioxaoctanoic acid, Fmoc-deprotection, second coupling with Fmoc-8-amino-3,6-dioxa-octanoic acid and Fmoc-deprotection as depicted above and described in "Materials and Methods".

Correct product was confirmed by cleavage of a small amount of resin as described in "Materials and Methods" and MS analysis.

MS: m/z 906.5=[M+H]$^+$ (calculated=906.5 g/mol).

Example 9

Synthesis of PEG-Pramipexole Conjugates (9a), (9b), (9c), (9d), and (9e)

Yield: 3.2 mg (0.003 mmol, TFA salt).
MS: m/z 931.4=[M+H]$^+$, (calculated=932.1 g/mol).
9b was synthesized as described for 9a except for the use of 2b (1.8 mg, 0.003 mmol) instead of 1b.
Yield: 3.3 mg (0.003 mmol, TFA salt).
MS: m/z 987.5=[M+H]$^+$, (calculated=987.5 g/mol).
9c was synthesized as described for 9a except for the use of 3b (2 mg, 0.004 mmol) instead of 1b.
Yield: 4.2 mg (0.004 mmol, TFA salt).
MS: m/z 1003.5=[M+H]$^+$, (calculated=1004.3 g/mol).
9d was synthesized as described for 9a except for the use of 4b (2 mg, 0.003 mmol) instead of 1b.
Yield: 1.8 mg (0.0015 mmol, double TFA salt).

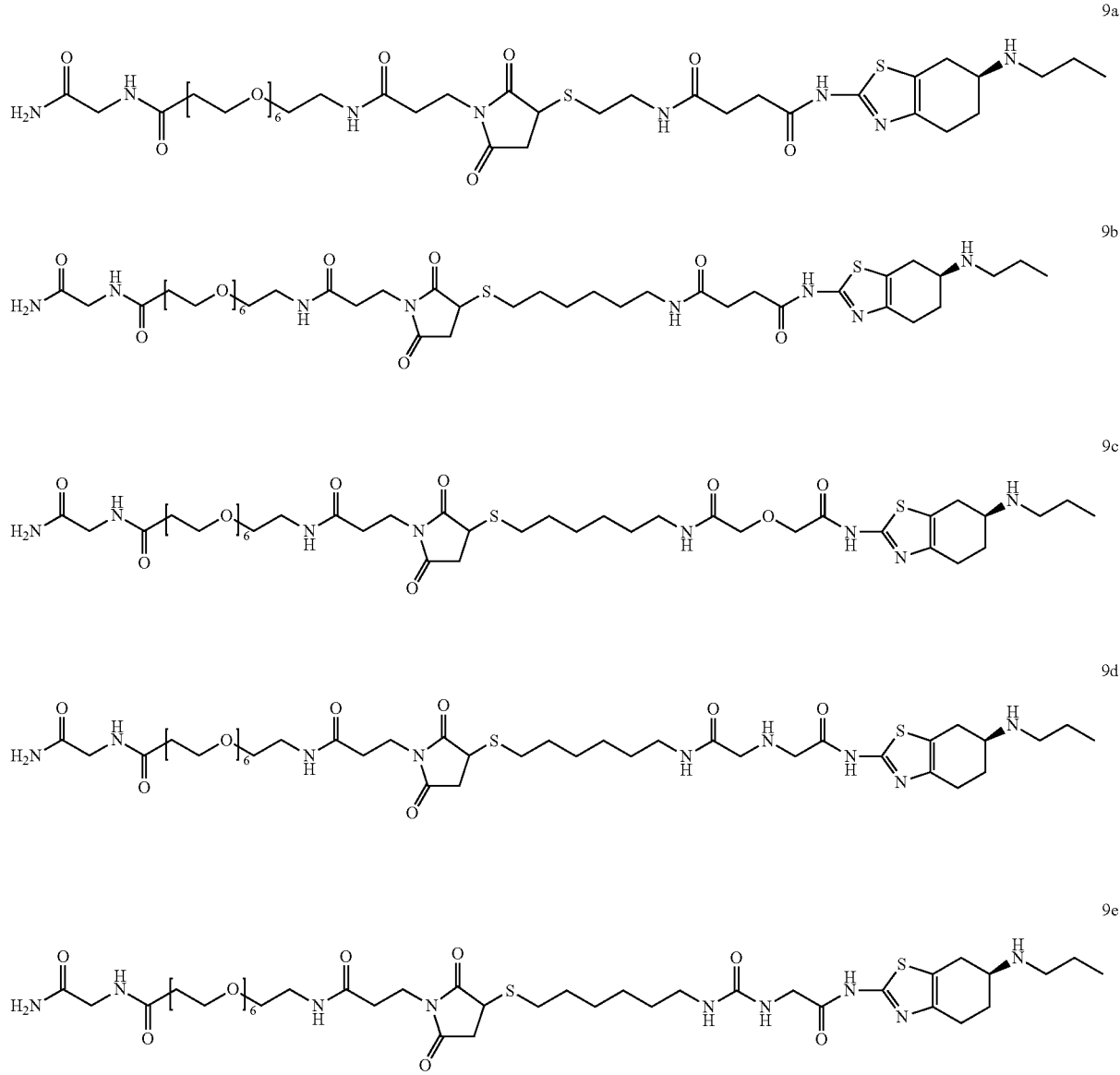

7 (4.5 mg, 0.008 mmol) and 1b (2 mg, 0.004 mmol) were dissolved in 1/1 acetonitrile/water (197 μL). 0.5 M phosphate buffer pH 7.4 (23 μL) was added and the solution aggitated for 10 min at RT. The mixture was acidified by addition of acetic acid, diluted with water (200 μL), and 9a was purified by RP-HPLC.

MS: m/z 1002.5=[M+H]$^+$, (calculated=1003.3 g/mol).

9e was synthesized as described for 9a except for the use of 5b (2 mg, 0.004 mmol) instead of 1b.

Yield: 3.4 mg (0.003 mmol, TFA salt).

MS: m/z 988.5=[M+H]$^+$, (MW calculated=989.3 g/mol).

Example 10

Synthesis of OEG-linker Pramipexole Conjugate (10)

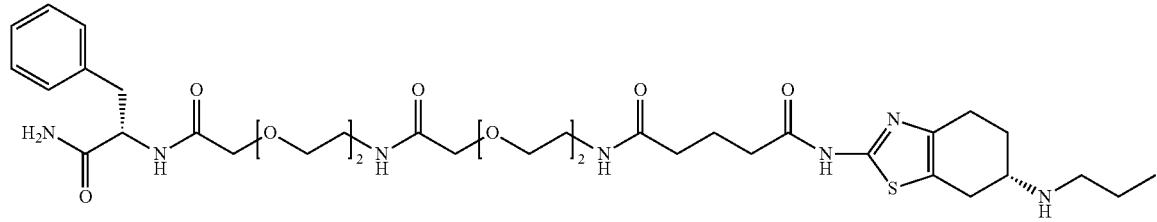

For the synthesis of PEG-pramipexole conjugate 10 resin 8 (25 mg, 0.012 mmol) was coupled with 6 (5.4 mg, 0.012 mmol) and the product was cleaved from the resin as described in "Materials and Methods". 10 was purified by RP-HPLC.

Yield: 3.9 mg (0.003 mmol, TFA salt).
MS: m/z 1213.7=[M+H] (calculated=1213.9 g/mol).

Example 11

Synthesis of Backbone Reagents (12g) and (12h)

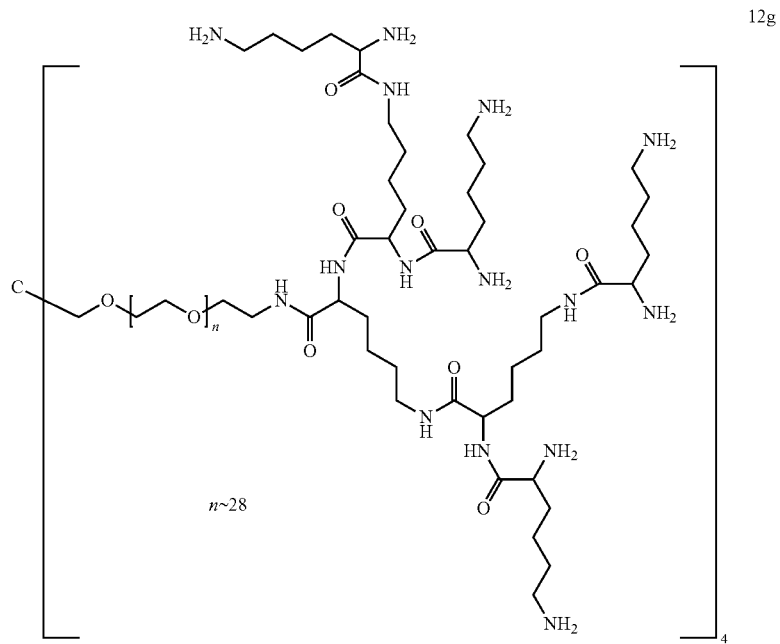

Backbone reagent 12g was synthesized from Amino 4-arm PEG5000 12a according to following scheme:

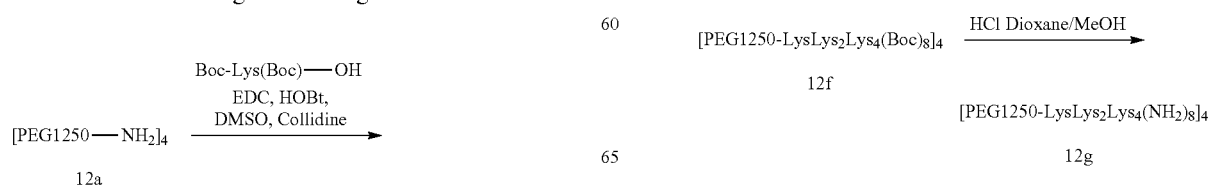

[PEG1250—NH$_2$]$_4$
12a $\xrightarrow{\text{Boc-Lys(Boc)—OH, EDC, HOBt, DMSO, Collidine}}$

[PEG1250-Lys(Boc)$_2$]$_4$
12b $\xrightarrow{\text{HCl Dioxane/MeOH}}$

[PEG1250K-Lys(NH$_2$)$_2$]$_4$
12c $\xrightarrow{\text{Boc-Lys(Boc)—OH}}$

[PEG1250-LysLys$_2$(Boc)$_4$]$_4$
12d $\xrightarrow{\text{HCl Dioxane/MeOH}}$

[PEG1250-LysLys$_2$(NH$_2$)$_4$]$_4$
12e $\xrightarrow{\text{Boc-Lys(Boc)—OH}}$

12g

[PEG1250-LysLys$_2$Lys$_4$(Boc)$_8$]$_4$
12f $\xrightarrow{\text{HCl Dioxane/MeOH}}$

[PEG1250-LysLys$_2$Lys$_4$(NH$_2$)$_8$]$_4$
12g

For synthesis of compound 12b, 4-Arm-PEG5000 tetraamine 12a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt.H$_2$O (0.96 g, 6.25 mmol), and collidine (5.20 mL, 40 mmol) were added. The reaction mixture was stirred for 30 min at RT.

The reaction mixture was diluted with 1200 mL of dichloromethane and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 12b as colorless oil. Compound 12b was purified by RP-HPLC.

Yield 3.85 g (59%) colorless glassy product 12b.
MS: m/z 1294.4=[M+5H]$^{5+}$ (calculated=1294.6).

Compound 12c was obtained by stirring of 3.40 g of compound 12b (0.521 mmol) in 5 mL of methanol and 9 mL of 4 N HCl in dioxane at RT for 15 min. Volatiles were removed in vacuo. The product was used in the next step without further purification.
MS: m/z 1151.9=[M+5H]$^{5+}$ (calculated=1152.0).

For synthesis of compound 12d, 3.26 g of compound 12c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 12d, which was used in the next step without further purification.
MS: m/z 1405.4=[M+6H]$^{6+}$ (calculated=1405.4).

Compound 12e was obtained by stirring a solution of compound 12d (3.96 g, 0.47 mmol) in 7 mL of methanol and 20 mL of 4 N HCl in dioxane at RT for 15 min. Volatiles were removed in vacuo. The product was used in the next step without further purification.
MS: m/z 969.6=[M+7H]$^{7+}$ (calculated=969.7).

For the synthesis of compound 12f, compound 12e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 12f as colorless oil.

Product was dissolved in DCM and precipitated with cooled (−18° C.) diethylether. This step was repeated twice and the precipitate was dried in vacuo.

Yield 4.72 g (82%) colourless glassy product 12f which was used in the next step without further purification.
MS: m/z 1505.3=[M+8H]$^{8+}$ (calculated=1505.4).

Backbone reagent 12g was obtained by stirring a solution of compound 12f (MW ca 12035 g/mol, 4.72 g, 0.39 mmol) in 20 mL of methanol and 40 mL of 4 N HCl in dioxane at RT for 30 min. Volatiles were removed in vacuo.

Yield 3.91 g (100%), glassy product backbone reagent 12g.
MS: m/z 977.2=[M+9H]$^{9+}$ (calculated=977.4).

Synthesis of Backbone Reagent 12h

[PEG500-LysLys$_2$Lys$_4$(NH$_2$)$_8$]$_4$

12h
=

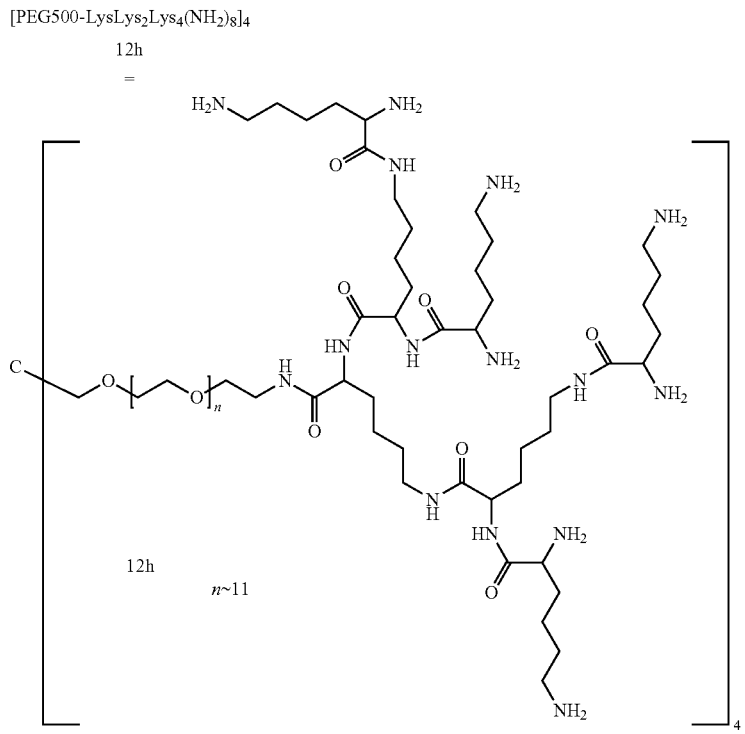

12h
$n \sim 11$

Backbone reagent 12h was synthesized as described for 12g except for the use of 4-arm PEG2000 instead of 4-arm PEG5000.

MS: m/z 719.4=[M+9H]$^{8+}$ (calculated=719.5).

Example 12

Synthesis of Crosslinker Reagents (13d), (13e), and (13f)

Crosslinker reagent 13d was prepared from adipic acid mono benzyl ester (English, Arthur R. et al., *Journal of Medicinal Chemistry*, 1990, 33(1), 344-347) and PEG2000 according to the following scheme:

sation was complete. The crystalline product was filtered through a glass frit and washed with cooled ether (−30° C.). The filter cake was dried in vacuo. Yield: 11.6 g (86%) 13b as a colorless solid. The product was used without further purification in the next step.

MS: m/z 813.1=[M+3H]$^{3+}$ (calculated=813.3)

In a 500 mL glass autoclave PEG2000-bis-adipic acid-bis-benzyl ester 13b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent

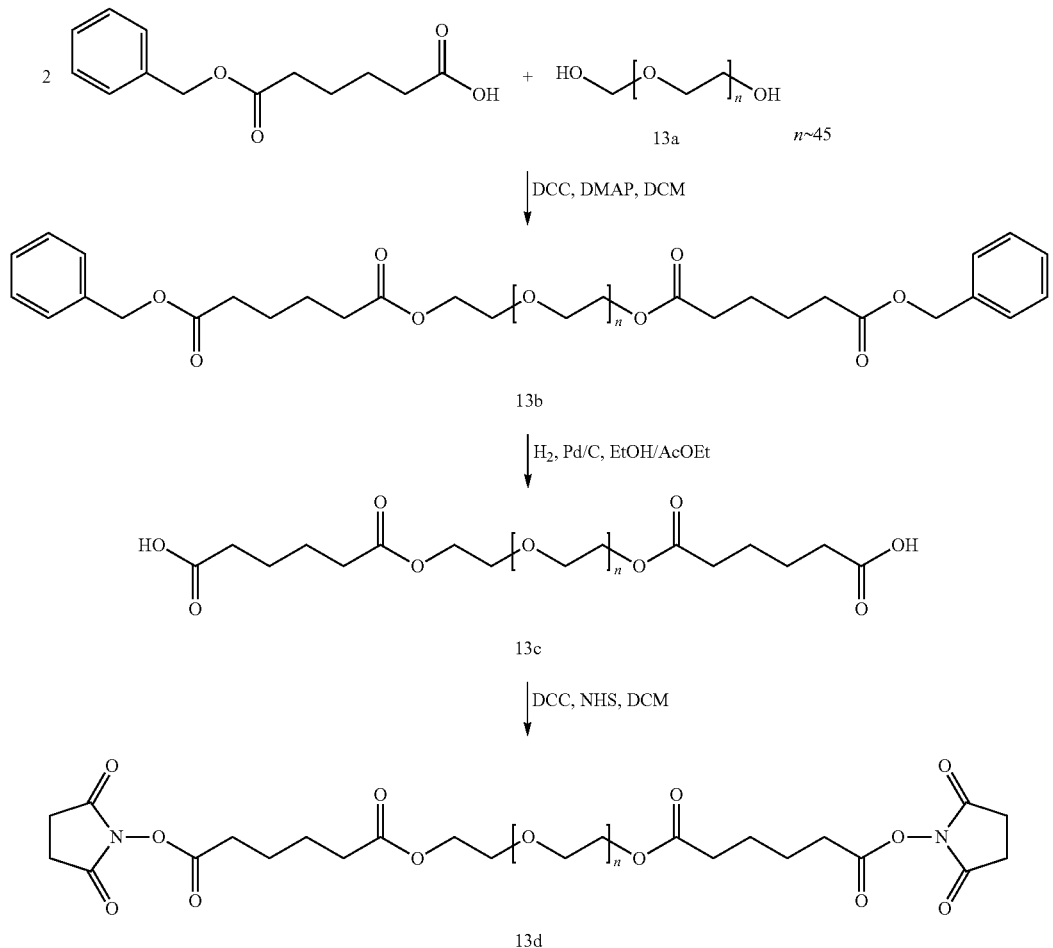

A solution of PEG2000 (13a) (11.0 g, 5.5 mmol) and benzyl adipate half-ester (4.8 g, 20.6 mmol) in dichloromethane (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by destillation in vacuo. The residue was dissolved in 1000 mL 1/1(v/v) ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystalliwas evaporated in vacuo. Yield: 12.3 g (quantitative) 13c as yellowish oil. The product was used without further purification in the next step.

MS: m/z 753.1=[M+3H]$^{3+}$ (calculated=753.2)

A solution of PEG2000-bis-adipic acid half ester 13c (9.43 g, 4.18 mmol), N-hydroxysuccinimide (1.92 g, 16.7 mmol) and DCC (3.44 g, 16.7 mmol) in 75 mL of DCM (anhydrous) was stirred over night at room temperature. The reaction mixture was cooled to 0° C. and precipitate was filtered off. DCM was evaporated and the residue was recrystallized from THF.

Yield: 8.73 g (85%) crosslinker reagent 13d as colorless solid.

MS: m/z 817.8=[M+3H]$^{3+}$ (calculated=817.9).

Synthesis of 13e

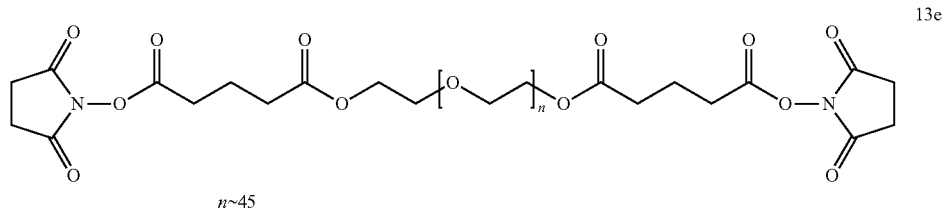

n~45

13e was synthesized as described for 13d except for the use of glutaric acid instead of adipic acid MS: m/z 764.4=[M+3H]$^{3+}$ (calculated=764.5).

Synthesis of 13f

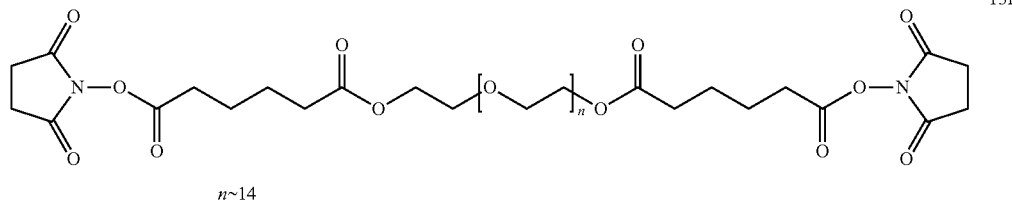

n~14

13f was synthesized as described for 13d except for the use of PEG600 instead of PEG2000

MS: m/z 997.5=[M+H]$^{+}$ (calculated=997.8)

Example 13

Preparation of Hydrogel Beads (14a), (14b), and (14c) Containing Free Amino Groups A solution of 300 mg 12g and 900 mg 13d in 10.8 mL DMSO was added to a solution of 100 mg Arlacel P135 (Croda International Plc) in 60 mL heptane. The mixture was stirred at 700 rpm with a custom metal stirrer for 10 min at RT to form a suspension. 1.1 mL N,N,N',N'-tertramethylene diamine (TMEDA) was added to effect polymerization. After 2 h, the stirrer speed was reduced to 400 rpm and the mixture was stirred for additional 16 h. 1.6 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 14a as a white powder.

14b was prepared as described for 14a except for the use of 322 mg 12h, 350 mg 13f, 2.9 ml DMSO, 1.6 ml TMEDA, 2.4 ml acetic acid and a stirring speed of 1000 rpm.

14c was prepared as described for 14a except for the use of 300 mg 12g, 810 mg 13e, 6.3 ml DMSO, 1.1 ml TMEDA, 1.6 ml acetic acid and a stirring speed of 1000 rpm.

Example 14

Preparation of Maleimide Functionalized Hydrogel Beads (15a) and (15b) and Determination of Maleimide Substitution A solution of 600 mg Mal-dPEG$_6$-NHS (1.0 mmol) in 4.5 mL 2/1 (v/v) acetonitrile/water was added to 200 mg dry hydrogel beads 14a. 500 μL sodium phosphate buffer (pH 7.4, 0.5 M) was added and the suspension was agitated for 30 min at room temperature. Beads 15a were washed five times each with 2/1 (v/v) acetonitrile/water, methanol and 1/1/0.001 (v/v/v/) acetonitrile/water/TFA.

For determination of maleimide content, an aliquot of hydrogel beads 15a was lyophilized and weighed out. Another aliquot of hydrogel beads 15a was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). Maleimide content was determined to be 0.27 mmol/g dry hydrogel.

15b was prepared as described above except for the use of 14b instead of 14a.

Loading 15b: 0.9 mmol/g

Example 15

Synthesis of Hydrogel-linker-pramipexole Conjugate (16a) and (16b)

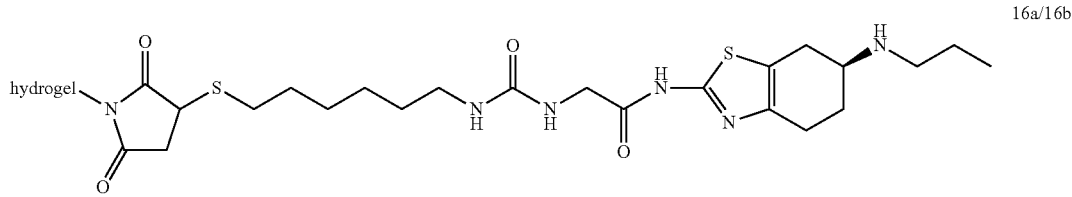

Maleimide-derivatized hydrogel microparticles 15a (100 μL. loading 30 μmol/mL, 3 mmol) were reacted with compound 5b (2.3 mg, 4.3 μmol) in 1/1 acetonitrile/water (420 μL) and 0.5 M phosphate buffer pH 7.4 (52 μL) for 10 min at RT. The hydrogel was washed 20 times with 1/1 acetonitrile/water. Remaining maleimides where reacted with 2-mercaptoethanol (34 μL, 0.48 mmol) in 1/1 acetonitrile/water (3 mL) and 0.5 M phosphate buffer pH 7.4 (0.4 mL) for 10 min at RT. The loaded hydrogel was washed 20 times with 1/1 acetonitrile/water, 20 times with phosphate buffer pH 7.4 and incubated in the same buffer (1.5 mL) at 37° C.

Pramipexole loading 16a: 27 mg/g

High loaded pramipexole linker hydrogel 16b was prepared as described above except for the use of 88 mg 5b and 100 mg 14b.

Pramipexole loading 16b: 152 mg/g

Example 16

Release Kinetics in vitro

Release of drug molecule from 9a, 9b, 9c, 9d, 9e, 10, 16a, and 16b was effected by hydrolysis in buffer at pH 7.4 and 37° C.

9a, 9b, 9c, 9d, 9e, and 10, respectively, were dissolved in buffer (60 mM sodium phosphate, 3 mM EDTA, 0.01% Tween20, pH 7.4), solution was filtered through a 0.2 μm filter and incubated at 37° C. Samples were taken at time intervals and analyzed by RP-HPLC at 263 nm and 280 nm and ESI-MS. UV-signals correlating to linker conjugate molecules were integrated and plotted against incubation time. Curve-fitting software was applied to estimate the corresponding half time of release 16a and 16b, respectively, were suspended in buffer (60 mM sodium phosphate, 3 mM EDTA, 0.01% Tween20, pH 7.4) and incubated at 37° C. At time intervals samples were suspended, centrifuged and samples (10-50 μL) were taken from the supernatant solution. Samples were diluted with buffer and analyzed by measurement of the absorption of released drug at 262 nm. Calculated amounts of released drug were plotted against incubation time.

Curve-fitting software was applied to estimate the corresponding half time of release.

FIG. 1 additionally depicts the in vitro release kinetic of the carrier linked pramipexole prodrug of example 16a. The x-axis shows the time [unit: days].

| Compound | $t_{1/2}$ buffer A (pH 7.4) |
| --- | --- |
| 9a | 1.2 d |
| 9b | 3.7 d |
| 9c | 1.3 d |
| 9d | 1.1 d |
| 9e | 4.3 d |
| 10 | 100 d |
| 16a | 5.1 d |
| 16b | 15 d |

Abbreviations

AcOH acetic acid
Ado 8-amino-3,6-dioxa-octanoic acid
Boc t-butyloxycarbonyl
DBU 1,3-diazabicyclo[5.4.0]undecene
DCC dicyclohexylcarbodiimide
DCM dichloromethane
DIC diisopropyl carbodiimide
DIEA diisopropylethylamine
DMAP dimethylamino-pyridine
DMF N,N-dimethylformamide
DMSO dimethylsulfoxide
EDC 1-Ethyl-3-(3-dimethylaminopropyl)carbodiimid
EDTA ethylenediaminetetraacetic acid
ESI electrospray ionization
EtOH ethanol
eq stoichiometric equivalent
Fmoc 9-fluorenylmethoxycarbonyl
HATU O-(7-Azabenzotriazol-1-yl)-N,N,N',N'-tetramethyluronium hexafluorophosphate
HFIP hexafluoroisopropanol
HOBt N-hydroxybenzotriazole
LCMS mass spectrometry-coupled liquid chromatography
Mal 3-maleimido propionyl
Mal-dPEG$_6$-NHS N-(3-maleimidopropyl)-21-amino-4,7,10,13,16,19-hexaoxa-heneicosanoic acid NHS ester
MS mass spectrum/mass spectrometry NHS N-hydroxy succinimide
OEG Oligo(ethylene glycol)
PEG poly(ethylene glycol)
PyBOP benzotriazole-1-yl-oxy-tris-pyrrolidino-phosphonium hexafluorophosphate
RP-HPLC reversed-phase high performance liquid chromatography
RT room temperature
TCP 2-chlorotrityl chloride resin
TES triethylsilane
TFA trifluoroacetic acid
THF tetrahydrofurane
TMEDA N,N,N',N', tetramethyl ethylene diamine
Trt trityl
UPLC ultra performance liquid chromatography
UV ultraviolet
VIS visual

The invention claimed is:
1. A prodrug or a pharmaceutically acceptable salt thereof comprising
  a drug linker conjugate D-L:
  wherein:
    D is an aromatic amine containing biologically active moiety; and
    L is a non-biologically active linker containing
      i) a moiety L$^1$ represented by formula (I):

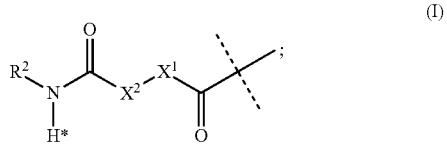

(I)

wherein:
  the dashed line indicates the attachment of L$^1$ to an aromatic amino group of D by forming an amide bond;
  X$^1$ is C(R$^1$R$^{1a}$) or a cyclic fragment selected from the group consisting of C$_{3-7}$ cycloalkyl, 4 to 7 membered heterocyclyl, phenyl, naphthyl, indenyl, indanyl, tetralinyl, and 9 to 11 membered heterobicyclyl, wherein:
    in case X$^1$ is a cyclic fragment, said cyclic fragment is incorporated into L$^1$ via two adjacent ring atoms and the ring atom of $X^1$, which is adjacent to the carbon atom of the amide bond, is also a carbon atom;

$X^2$ is a chemical bond or selected from $C(R^3R^{3a})$, $N(R^3)$, O, $C(R^3R^{3a})$—$C(R^4R^{4a})$, $C(R^3R^{3a})$—N($R^4$), $N(R^3)$—$C(R^4R^{4a})$, $C(R^3R^{3a})$—O, or O—$C(R^3R^{3a})$, wherein:

in case $X^1$ is a cyclic fragment, $X^2$ is a chemical bond, $C(R^3R^{3a})$, $N(R^3)$, or O;

optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;

$R^1$, $R^3$, and $R^4$ are independently selected from the group consisting of H, $C_{1-4}$ alkyl, and —$N(R^5R^{5a})$;

$R^{1a}$, $R^2$, $R^{3a}$, $R^{4a}$, and $R^{5a}$ are independently selected from the group consisting of H and $C_{1-4}$ alkyl;

$R^5$ is $C(O)R^6$; and $R^6$ is $C_{1-4}$ alkyl; and optionally, one of the pairs $R^{1a}/R^{4a}$, $R^{3a}/R^{4a}$ or $R^{1a}/R^{3a}$ form a chemical bond; and ii) a moiety $L^2$, which is a chemical bond or a spacer, where $L^2$ is bound to a polymeric carrier group Z;

wherein $L^1$ is substituted with one to four $L^2$ moieties, provided that the hydrogen marked with the asterisk in formula (I) is not replaced by $L^2$; and wherein, optionally, L is further substituted.

2. The prodrug according to claim 1;

wherein, in the moiety $L^1$ represented by formula (I):

$X^1$ is $C(R^1R^{1a})$, cyclohexyl, phenyl, pyridinyl, norbonenyl, furanyl, pyrrolyl, or thienyl, wherein:

in case $X^1$ is a cyclic fragment, said cyclic fragment is incorporated into $L^1$ via two adjacent ring atoms;

$X^2$ is a chemical bond or selected from the group consisting of $C(R^3R^{3a})$, $N(R^3)$, O, $C(R^3R^{3a})$—O, and $C(R^3R^{3a})$—$C(R^4R^{4a})$;

$R^1$, $R^3$, and $R^4$ are independently selected from the group consisting of H, $C_{1-4}$ alkyl, and —$N(R^5R^{5a})$;

$R^{1a}$, $R^{3a}$, $R^{4a}$, and $R^{5a}$ are independently selected from the group consisting of H and $C_{1-4}$ alkyl;

$R^2$ is $C_{1-4}$ alkyl;

$R^5$ is $C(O)R^6$; and $R^6$ is $C_{1-4}$ alkyl.

3. The prodrug according to claim 1;

wherein the moiety $L^1$ is selected from:

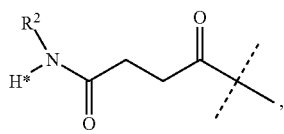

(i)

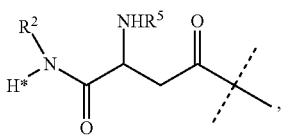

(ii)

-continued

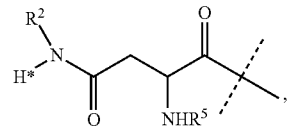

(iii)

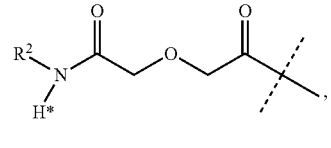

(iv)

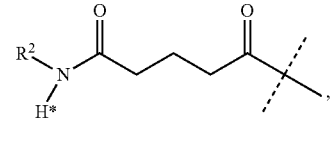

(v)

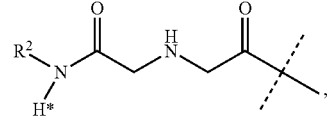

(vi)

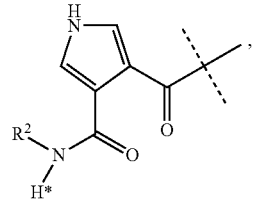

(vii)

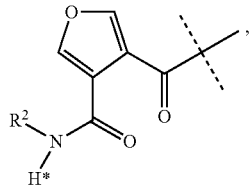

(viii)

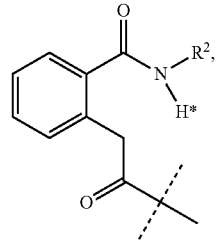

(ix)

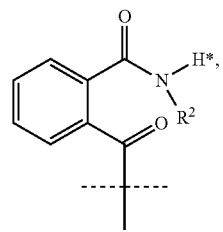

(x)

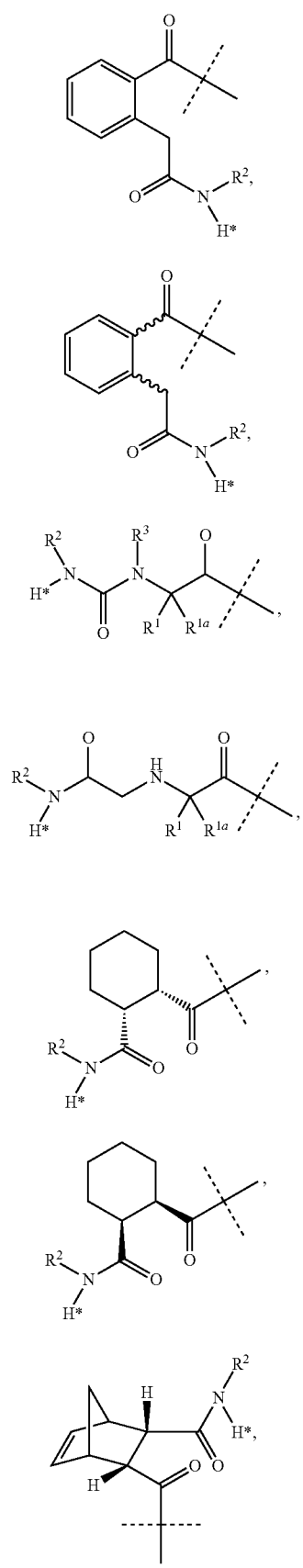
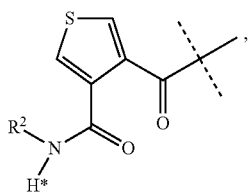
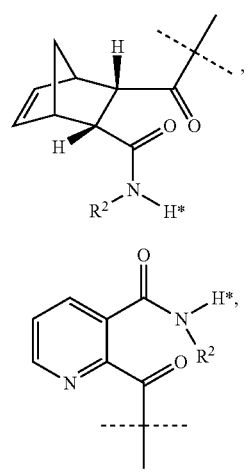
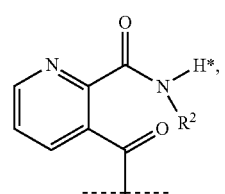
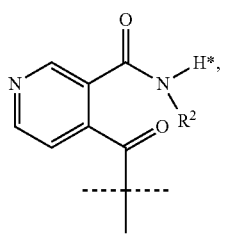
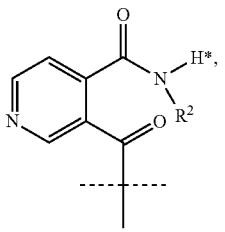
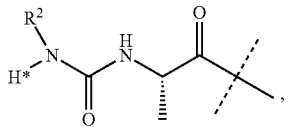

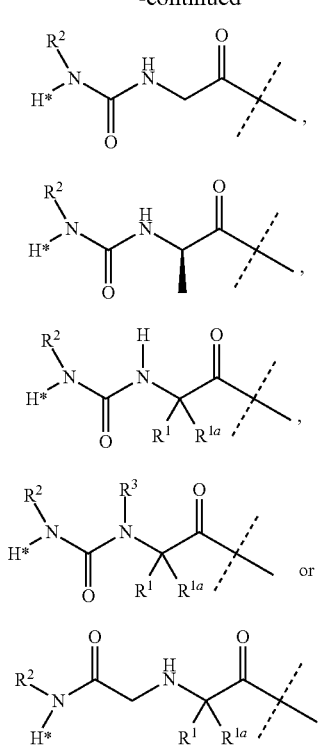

wherein:
R⁵ is C(O)R⁶;
R¹, R¹ᵃ, R², R³, and R⁶ are independently from each other C$_{1-4}$ alkyl; and
L¹ is substituted with one L² moiety; and
optionally R² is substituted with one L² moiety.

4. The prodrug according to claim 1;
wherein the spacer is a fragment selected from C$_{1-50}$ alkyl, C$_{2-50}$ alkenyl or C$_{2-50}$ alkinyl, which fragment is optionally interrupted by one or more groups selected from —NH—, —N(C$_{1-4}$ alkyl)-, —O—, —S—, —C(O)—, —C(O)NH—, —C(O)N(C$_{1-4}$ alkyl)-, —O—C(O)—, —S(O)—, —S(O)$_2$—, 4 to 7 membered heterocyclyl, phenyl or naphthyl, provided that the spacer does not contain a nitrogen atom being in β- or γ-position to the amino group containing the hydrogen marked with the asterisk in formula (I), in case the spacer is bound to R².

5. The prodrug according to claim 1;
wherein L² is a chemical bond.

6. The prodrug according to claim 1;
wherein the carrier group Z is a polymer with a molecular weight ≥500 g/mol.

7. The prodrug according to claim 1;
wherein L¹ is substituted with one L² and the carrier group Z is a biodegradable polyethylene glycol based water-insoluble hydrogel.

8. The prodrug according to claim 1;
wherein the aromatic amine containing biologically active moiety D is derived from the corresponding biologically active drug D-H, which is selected from the group consisting of:

Abacavir, Acadesine, Acediasulfone, Aciclovir, Actimid, Actinomycin, Adefovir, Aditeren, Afloqualone, Aztreonam,Adefovir Dipivoxil, Adenine, Adenosine, Adenosine monophosphate, Adenosine triphosphate, Alfuzosin, Alpiropride, Ambasilide, Ambucaine, Ameltolide, Amethopterin, Amicycline, Amidapsone, Amiloride, Aminoacridine, Aminoantipyrine, Aminobenzoate, 6-Aminoflavone, 17-Aminogeldanamycin, Aminogenistein, Aminoglutethimide, Aminohippurate, 3'-Amino-4'-methoxyflavone, Aminonimetazepam, Aminopotentidine, Amphenidone, N-(p-Aminophenethyl)spiroperidol, 2-Amino-6(5H)-phenanthridinone, Amiphenosine, Aminophenylalanine, Aminopterin, Aminopurvalanol A, Amfenac, Amiphenazole, Amphotalide, Aminoisatin, Arninosalicylic Acid, Amifampridine, Amisulpride, Amlexanox, Amonafide, Amprenavir, Amrinone, Amthamine, Anileridine, Apraclonidine, Ascensil, Atolide, Azabon, Azacitidine, Azepexole, Aztreonam, Basedol, Benzocaine, Batanopride, Betoxycaine, Bleomycin, Bromfenac, Bromobuterol, Bromopride, Carbutamide, Carumonam, Candicidin, Cefepime, Cefcapene pivoxil, Cefdaloxime, Cefdinir, Cefditoren, Cefempidone, Cefetamet, Cefepime, Cefetecol, Cefixime, Cefmatilen, Cefmenoxime, Cefodizime, Cefoselis, Cefotaxime, Cefotiam, Ceftiolene, Ceftioxide, Cefpodoxime, Cefquinome, Cefrom, Ceftazidime , Cefteram, Ceftibuten, Ceftiofur, Ceftizoxime, Ceftriaxone, Cefuzonam, Cisapride, Clenproperol, Chloroprocaine, Cidofovir, Cisapride, Cladribine, Clafanone, Claforan, Clebopride, Clenbuterol, Clofarabine, Clorsulon, Cycloclenbuterol, Cytarabine, Cytidoline, Dactinomycin, Daniquidone, Dactinomycin, Dapsone, Daptomycin, Daraprim, Darunavir, Dazopride, Decitabine, Dedopramide, Diaminoacridine, Dichlorophenarsine, Dimethocaine, 10'-Demethoxystreptonigrin, 2,7-Dimethylproflavine, Dinalin, Dobupride, Doxazosin, Draflazine, Emtricitabine, Entecavir, Ethacridine, Etanterol, Etoxazene, Famciclovir, Fepratset, (±)-FLA 668, Flucytosine, Fludarabine, Folic Acid, Fosamprenavir, Ganciclovir, Gemcitabine, Gloximonam, GSK 3B Inhibitor XII, Glybuthiazol, Hydroxyrnethylclenbuterol, Hydroxyprocaine, Imiquimod, Indanocine, Iomeglamic acid, Iramine, Isobutamben, Isoritmon, Ketoclenbuterol, Lamivudine, Lamotrigine, Lavendamycin, Lenalidomide, Leucinocaine, Leucovorin, Lintopride, Lisadimate, Mabuterol, Medeyol, Mesalazine, Metabutethamine, Metabutoxycaine, Metahexamide, Methyl anthranilate, Methotrexate, Metoclopramide, Minoxidil, Mirabegron, Mitomycin, Mocetinostat, Monocain, Mosapride, NADH, Mutamycin, Naepaine, Naminterol, Nelarabine, Nepafenac, Nerisopam, Nitrine, Nomifensine, Norcisapride, Olamufloxacin, Orthocaine, Oxybuprocaine, Oximonam, Pancopride, Parsalmide, Pathocidine, Pasdrazide, Pemetrexed, Penciclovir, Phenazone, Phenazopyridine, Phenyl-PAS-Tebamin, Picumeterol, Pirazmonam, Porfiromycin, Pramipexole, Prazosin, Piridocaine, Procainamide, Procaine, Proflavine, N-Propionylprocainamide, Proparacaine, Propoxycaine, Prucalopride, Pyrimethamine, Questiomycin, Renoquid, Renzapride, Retigabine, Riluzole, Rufocromomycin, S-Adenosylrnethionine, Silver sulfadiazine, Sparfloxacin, Stearylsulfamide, Streptonigrin, Succisulfone, Sulamserod, Sulfabromomethazine, Sulfacetamide, Sulfaclozine, Sulfaclorazole, Sulfachlorpyridazine, Sulfachrysoidine, Sulfaclomide, Sulfacytine, Sulfadiasulfone, Sulfadimethoxine, Sulfadimidine, Sulfadicramide, Sulfadiazine, Sulfadoxine, Sulfaguanidine, Sulfaguanole, Sulfalene, Sulfamerazine, Sulfamethazine, Sulfanilamidoimidazole, Sulfanilylglycine, N-Sulfanilylnorfloxacin, Sulfathiadiazole, Sulfamethizole, Sulfamethoxazole, Sulfametopyrazine, Sulfapyrazole, Sulfamethoxydiazine, Sulfasymazine, Sulfatrozole, Sulfatroxazole, Sulfamethoxypyridazine, Sulfametomidine, Sulfametrole, Sufamonomethoxine, Sulfanilamide, Sulfaperin, Sulfaphenazole, Sulfaproxyline, Sulfapyridine, Sulfisomidine, Sulfasomizole, Sulfisoxazole, Suprax, Tacedinaline, Tacrine, Talampanel, Talipexole, Tenofovir, Terazosin, Tetrahydrobiopterin, Tetrahydrofolic acid, Thiamine, Thiazosulfone, Thioguanine, Tigemonam, Timirdine, Trimethoprim, Triamterene, Trimethoprim, Trimetrexate, Tritoqualine, Valaciclovir, Valganciclovir, Veradoline, Vidarabine, Zalcitabine, and Zoxazolamine.

9. The prodrug according to claim 8;
wherein D-H is pramipexole.

10. A pharmaceutical composition comprising;
an effective dose of at least one prodrug or a pharmaceutically acceptable salt thereof according to claim 1; and
a pharmaceutically acceptable excipient.

11. The composition according to claim 10;
wherein the polymer is polyethylene glycol or a polyethylene glycol-based hydrogel, preferably polyethylene glycol-based hydrogel microparticles with a particle diameter of 10 to 1000 microns, preferably 15 to 100 microns.

12. The composition according to claim 10;
wherein the polymer is a polyethylene glycol-based hydrogel with a particle diameter of 10 to 1000 microns, preferably 15 to 100 microns.

13. The composition of claim 10;
wherein the prodrug can be administered by injection through a needle smaller than 0.6 mm inner diameter.

14. The composition of claim 13;
wherein the needle is smaller than 0.3 mm inner diameter.

15. The composition of claim 13;
wherein the needle is smaller than 0.25 mm.

16. A method for treatment of a dopamine receptor related disease, including Parkinson's disease, neurological disorders, amyotrophic lateral sclerosis, compulsive behavior, bipolar disorders, Tourette's syndrome, depressive disorders, treatment resistant depression, fibromyalia or restless leg syndrome (RLS), comprising:
utilizing a prodrug of claim 1.

17. The method according to claim 16;
wherein the disease is Parkinsons's disease or RLS.

18. A method for treatment of a dopamine receptor related disease, including Parkinson's disease, neurological disorders, amyotrophic lateral sclerosis, compulsive behavior, bipolar disorders, Tourette's syndrome, depressive disorders, treatment resistant depression, fibromyalia or restless leg syndrome (RLS), comprising:
utilizing a pharmaceutical composition of claim 10.

19. The method of claim 18;
wherein the disease is Parkinsons's disease or RLS.

20. A method for the synthesis of a prodrug or a pharmaceutically acceptable salt thereof according to claim 1, comprising:
reacting a prodrug precursor L-Y or $L^1$-Y with a biologically active drug D-H to obtain the drug linker conjugate D-L or a drug linker intermediate D-$L^1$ by forming an amide bond;
wherein Y is a leaving group.

* * * * *